US012667458B2

(12) United States Patent
Dvorsky

(10) Patent No.: US 12,667,458 B2
(45) Date of Patent: Jun. 30, 2026

(54) TAPERED PROSTHETIC HEART VALVES WITH VALVULAR STRUCTURES FORMING TAPERED FLOW CHANNELS

(71) Applicant: EDWARDS LIFESCIENCES CORPORATION, Irvine, CA (US)

(72) Inventor: Anatoly Dvorsky, Haifa (IL)

(73) Assignee: Edwards Lifesciences Corporation, Irvine, CA (US)

( * ) Notice: Subject to any disclaimer, the term of this patent is extended or adjusted under 35 U.S.C. 154(b) by 584 days.

(21) Appl. No.: 18/118,236

(22) Filed: Mar. 7, 2023

(65) Prior Publication Data

US 2023/0200985 A1 Jun. 29, 2023

Related U.S. Application Data

(63) Continuation of application No. PCT/US2021/049537, filed on Sep. 8, 2021.
(Continued)

(51) Int. Cl.
*A61F 2/24* (2006.01)
(52) U.S. Cl.
CPC ............ *A61F 2/2418* (2013.01); *A61F 2/243* (2013.01); *A61F 2230/0054* (2013.01)
(58) Field of Classification Search
CPC ................... A61F 2/2418; A61F 2/243; A61F 2230/0054; A61F 2/2439; A61F 2220/0091; A61F 2230/0067
See application file for complete search history.

(56) References Cited

U.S. PATENT DOCUMENTS

| | | | |
|---|---|---|---|
| 3,409,013 A | 11/1968 | Berry | |
| 3,548,417 A | 12/1970 | Ronnie et al. | |
| | (Continued) | | |

FOREIGN PATENT DOCUMENTS

| | | |
|---|---|---|
| DE | 0144167 C | 9/1903 |
| DE | 2246526 A1 | 3/1973 |
| | (Continued) | |

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suzette J Gherbi
(74) *Attorney, Agent, or Firm* — Klarquist Sparkman, LLP

(57) ABSTRACT

A prosthetic heart valve has a frame and a valvular structure coupled thereto. The valvular structure has multiple leaflets, with paired tabs from the leaflets forming commissure tab assemblies that couple the valvular structure to the frame. The frame is tapered with its inflow end diameter being smaller than its outflow end diameter. The valvular structure is constructed such that a flow channel formed by the leaflets is also tapered, with the inlet end cross-section being smaller than the outlet end cross-section. The commissure tab assemblies are attached to the frame with leaflet bending axes at or adjacent to the radially-inner surface of the frame. During systole, separation of blood flow induced by the tapered geometry of the flow channel generates an annular back flow region adjacent to the inner surface of the valve at the outflow end, which prevents the free edge of the leaflets from contacting the frame.

19 Claims, 16 Drawing Sheets

Related U.S. Application Data

(60)  Provisional application No. 63/076,293, filed on Sep. 9, 2020.

(56) References Cited

U.S. PATENT DOCUMENTS

| | | | |
|---|---|---|---|
| 3,587,115 A | 6/1971 | Donald | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,244 B2 | 4/2004 | Klaco | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,936,067 B2 | 8/2005 | Buchanan | |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,316,710 B1 | 1/2008 | Cheng et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |

(56)                     References Cited

U.S. PATENT DOCUMENTS

| | | | |
|---|---|---|---|
| 7,563,280 | B2 | 7/2009 | Anderson et al. |
| 7,585,321 | B2 | 9/2009 | Cribier |
| 7,618,446 | B2 | 11/2009 | Andersen et al. |
| 7,618,447 | B2 | 11/2009 | Case et al. |
| 7,655,034 | B2 | 2/2010 | Mitchell et al. |
| 7,785,366 | B2 | 8/2010 | Maurer et al. |
| 7,959,665 | B2 | 6/2011 | Pienknagura |
| 7,959,672 | B2 | 6/2011 | Salahieh et al. |
| 7,993,394 | B2 | 8/2011 | Hariton et al. |
| 8,029,556 | B2 | 10/2011 | Rowe |
| 8,075,611 | B2 | 12/2011 | Millwee et al. |
| 8,128,686 | B2 | 3/2012 | Paul et al. |
| 8,167,932 | B2 | 5/2012 | Bourang et al. |
| 8,291,570 | B2 | 10/2012 | Eidenschink et al. |
| 8,348,998 | B2 * | 1/2013 | Pintor ................... A61F 2/2418 |
| | | | 623/2.11 |
| 8,449,606 | B2 | 5/2013 | Eliasen et al. |
| 8,454,685 | B2 | 6/2013 | Hariton et al. |
| 8,652,203 | B2 | 2/2014 | Quadri et al. |
| 8,685,055 | B2 | 4/2014 | VanTassel et al. |
| 8,747,463 | B2 | 6/2014 | Fogarty et al. |
| 9,078,781 | B2 | 7/2015 | Ryan et al. |
| 11,224,509 | B2 | 1/2022 | Dasi et al. |
| 12,521,263 | B2 * | 1/2026 | Shelton ................. A61F 2/9525 |
| 2001/0021872 | A1 * | 9/2001 | Bailey ....................... A61F 2/07 |
| | | | 623/1.26 |
| 2002/0026094 | A1 | 2/2002 | Roth |
| 2002/0032481 | A1 | 3/2002 | Gabbay |
| 2002/0138135 | A1 | 9/2002 | Duerig et al. |
| 2002/0143390 | A1 | 10/2002 | Ishii |
| 2002/0173842 | A1 | 11/2002 | Buchanan |
| 2003/0014105 | A1 | 1/2003 | Cao |
| 2003/0040791 | A1 | 2/2003 | Oktay |
| 2003/0050694 | A1 | 3/2003 | Yang et al. |
| 2003/0100939 | A1 | 5/2003 | Yodfat et al. |
| 2003/0158597 | A1 | 8/2003 | Quiachon et al. |
| 2003/0212454 | A1 | 11/2003 | Scott et al. |
| 2004/0024452 | A1 | 2/2004 | Kruse et al. |
| 2004/0039436 | A1 | 2/2004 | Spenser et al. |
| 2004/0078074 | A1 | 4/2004 | Anderson et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0010285 | A1 | 1/2005 | Lambrecht et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0096738 | A1 | 5/2005 | Cali et al. |
| 2005/0137686 | A1 | 6/2005 | Salahieh et al. |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0108090 | A1 | 5/2006 | Ederer et al. |
| 2006/0149350 | A1 | 7/2006 | Patel et al. |
| 2006/0183383 | A1 | 8/2006 | Asmus et al. |
| 2006/0229719 | A1 | 10/2006 | Marquez et al. |
| 2006/0259136 | A1 | 11/2006 | Nguyen et al. |
| 2006/0259137 | A1 | 11/2006 | Artof et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0112422 | A1 | 5/2007 | Dehdashtian |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2008/0021546 | A1 | 1/2008 | Patz et al. |
| 2008/0114442 | A1 | 5/2008 | Mitchell et al. |
| 2008/0125853 | A1 | 5/2008 | Bailey et al. |
| 2008/0154355 | A1 | 6/2008 | Benichou et al. |
| 2008/0183271 | A1 | 7/2008 | Frawley et al. |
| 2008/0208327 | A1 | 8/2008 | Rowe |
| 2008/0243245 | A1 | 10/2008 | Thambar et al. |
| 2008/0255660 | A1 | 10/2008 | Guyenot et al. |
| 2008/0275537 | A1 | 11/2008 | Limon |
| 2008/0294248 | A1 | 11/2008 | Yang et al. |
| 2009/0118826 | A1 | 5/2009 | Khaghani |
| 2009/0125118 | A1 | 5/2009 | Gong |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0299452 | A1 | 12/2009 | Eidenschink et al. |
| 2009/0319037 | A1 | 12/2009 | Rowe et al. |
| 2010/0004735 | A1 | 1/2010 | Yang et al. |
| 2010/0049313 | A1 | 2/2010 | Alon et al. |
| 2010/0082094 | A1 | 4/2010 | Quadri et al. |
| 2010/0100176 | A1 | 4/2010 | Elizondo et al. |
| 2010/0121436 | A1 * | 5/2010 | Tuval ................... A61F 2/2427 |
| | | | 623/2.17 |
| 2010/0168844 | A1 | 7/2010 | Toomes et al. |
| 2010/0185277 | A1 | 7/2010 | Braido et al. |
| 2010/0198347 | A1 | 8/2010 | Zakay et al. |
| 2010/0204781 | A1 | 8/2010 | Alkhatib |
| 2011/0015729 | A1 | 1/2011 | Jimenez et al. |
| 2011/0022157 | A1 | 1/2011 | Essinger et al. |
| 2011/0066224 | A1 | 3/2011 | White |
| 2011/0137397 | A1 | 6/2011 | Chau et al. |
| 2011/0218619 | A1 | 9/2011 | Benichou et al. |
| 2011/0319991 | A1 | 12/2011 | Hariton et al. |
| 2012/0030090 | A1 | 2/2012 | Johnston et al. |
| 2012/0089223 | A1 | 4/2012 | Nguyen et al. |
| 2012/0101571 | A1 | 4/2012 | Thambar et al. |
| 2012/0123529 | A1 | 5/2012 | Levi et al. |
| 2012/0259409 | A1 | 10/2012 | Nguyen et al. |
| 2013/0023985 | A1 | 1/2013 | Khairkhahan et al. |
| 2013/0046373 | A1 | 2/2013 | Cartledge et al. |
| 2013/0150956 | A1 | 6/2013 | Yohanan et al. |
| 2013/0166017 | A1 | 6/2013 | Cartledge et al. |
| 2013/0190857 | A1 | 7/2013 | Mitra et al. |
| 2013/0245753 | A1 * | 9/2013 | Alkhatib ............... A61F 2/2418 |
| | | | 623/2.18 |
| 2013/0274873 | A1 | 10/2013 | Delaloye et al. |
| 2013/0304200 | A1 * | 11/2013 | McLean ................ A61F 2/2418 |
| | | | 623/2.18 |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0222136 | A1 | 8/2014 | Geist et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |
| 2014/0277563 | A1 | 9/2014 | White |
| 2014/0296962 | A1 | 10/2014 | Cartledge et al. |
| 2014/0330372 | A1 | 11/2014 | Weston et al. |
| 2014/0343670 | A1 | 11/2014 | Bakis et al. |
| 2014/0343671 | A1 | 11/2014 | Yohanan et al. |
| 2014/0350667 | A1 | 11/2014 | Braido et al. |
| 2015/0073545 | A1 | 3/2015 | Braido |
| 2015/0073546 | A1 | 3/2015 | Braido |
| 2015/0135506 | A1 | 5/2015 | White |
| 2015/0157455 | A1 | 6/2015 | Hoang et al. |
| 2016/0278922 | A1 * | 9/2016 | Braido ...................... A61F 2/89 |
| 2016/0374802 | A1 | 12/2016 | Levi et al. |
| 2017/0014229 | A1 | 1/2017 | Nguyen-Thien-Nhon et al. |
| 2018/0028310 | A1 | 2/2018 | Gurovich et al. |
| 2018/0153689 | A1 | 6/2018 | Maimon et al. |
| 2018/0206986 | A1 * | 7/2018 | Noe ...................... A61F 2/2409 |

(56) References Cited

U.S. PATENT DOCUMENTS

| | | | | |
|---|---|---|---|---|
| 2018/0325665 A1* | 11/2018 | Gurovich | ............. | A61F 2/2418 |
| 2018/0344456 A1 | 12/2018 | Barash et al. | | |
| 2019/0105153 A1* | 4/2019 | Barash | ................. | A61F 2/2418 |
| 2019/0159894 A1 | 5/2019 | Levi et al. | | |
| 2019/0192288 A1 | 6/2019 | Levi et al. | | |
| 2019/0192289 A1 | 6/2019 | Levi et al. | | |
| 2020/0197172 A1 | 6/2020 | Tuval et al. | | |
| 2023/0065795 A1* | 3/2023 | Zamani | ................. | A61F 2/2415 |
| 2023/0363903 A1* | 11/2023 | Dvorsky | .............. | A61F 2/2418 |
| 2025/0387227 A1* | 12/2025 | Srinimukesh | ......... | A61F 2/2412 |

FOREIGN PATENT DOCUMENTS

| | | | | |
|---|---|---|---|---|
| DE | 19532846 A1 | 3/1997 | | |
| DE | 19546692 A1 | 6/1997 | | |
| DE | 19857887 A1 | 7/2000 | | |
| DE | 19907646 A1 | 8/2000 | | |
| DE | 10049812 A1 | 4/2002 | | |
| DE | 10049813 C1 | 4/2002 | | |
| DE | 10049814 A1 | 4/2002 | | |
| DE | 10049815 A1 | 4/2002 | | |
| DE | 112022002277 B4 * | 10/2025 | ........... | A61F 2/2466 |
| EP | 0103546 B1 | 5/1988 | | |
| EP | 0850607 A1 | 7/1998 | | |
| EP | 1057460 A1 | 12/2000 | | |
| EP | 1088529 A2 | 4/2001 | | |
| EP | 1570809 A1 | 9/2005 | | |
| FR | 2788217 A1 | 7/2000 | | |
| FR | 2815844 A1 | 5/2002 | | |
| GB | 2056023 A | 3/1981 | | |
| SU | 1271508 A1 | 11/1986 | | |
| WO | 1991017720 A1 | 11/1991 | | |
| WO | 1992017118 A1 | 10/1992 | | |
| WO | 1993001768 A1 | 2/1993 | | |
| WO | 1997024080 A1 | 7/1997 | | |
| WO | 1998029057 A1 | 7/1998 | | |
| WO | 1999030646 A1 | 6/1999 | | |
| WO | 1999033414 A1 | 7/1999 | | |
| WO | 1999040964 A1 | 8/1999 | | |
| WO | 1999047075 A1 | 9/1999 | | |
| WO | 2000018333 A1 | 4/2000 | | |
| WO | 2000041652 A1 | 7/2000 | | |
| WO | 2000047139 A1 | 8/2000 | | |
| WO | 2001035878 A2 | 5/2001 | | |
| WO | 2001049213 A2 | 7/2001 | | |
| WO | 2001054624 A1 | 8/2001 | | |
| WO | 2001054625 A1 | 8/2001 | | |
| WO | 2001062189 A1 | 8/2001 | | |
| WO | 2001064137 A1 | 9/2001 | | |
| WO | 2001076510 A2 | 10/2001 | | |
| WO | 2002022054 A1 | 3/2002 | | |
| WO | 2002036048 A1 | 5/2002 | | |
| WO | 2002041789 A2 | 5/2002 | | |
| WO | 2002043620 A1 | 6/2002 | | |
| WO | 2002047575 A2 | 6/2002 | | |
| WO | 2002049540 A2 | 6/2002 | | |
| WO | 2003047468 A1 | 6/2003 | | |
| WO | 2005034812 A1 | 4/2005 | | |
| WO | 2005055883 A1 | 6/2005 | | |
| WO | 2005084595 A1 | 9/2005 | | |
| WO | 2005102015 A1 | 11/2005 | | |
| WO | 2006014233 A2 | 2/2006 | | |
| WO | 2006032051 A2 | 3/2006 | | |
| WO | 2006034008 A2 | 3/2006 | | |
| WO | 2006111391 A1 | 10/2006 | | |
| WO | 2006127089 A1 | 11/2006 | | |
| WO | 2006138173 A2 | 12/2006 | | |
| WO | 2007047488 A2 | 4/2007 | | |
| WO | 2007067942 A1 | 6/2007 | | |
| WO | 2007097983 A2 | 8/2007 | | |
| WO | 2008005405 A2 | 1/2008 | | |
| WO | 2008015257 A2 | 2/2008 | | |
| WO | 2008035337 A2 | 3/2008 | | |
| WO | 2008091515 A2 | 7/2008 | | |
| WO | 2008147964 A1 | 12/2008 | | |
| WO | 2008150529 A1 | 12/2008 | | |
| WO | 2009033469 A1 | 3/2009 | | |
| WO | 2009042196 A2 | 4/2009 | | |
| WO | 2009053497 A1 | 4/2009 | | |
| WO | 2009061389 A2 | 5/2009 | | |
| WO | 2009094188 A2 | 7/2009 | | |
| WO | 2009116041 A2 | 9/2009 | | |
| WO | 2009149462 A2 | 12/2009 | | |
| WO | 2010011699 A2 | 1/2010 | | |
| WO | 2010121076 A2 | 10/2010 | | |
| WO | 2013106585 A1 | 7/2013 | | |
| WO | 2015085218 A1 | 6/2015 | | |
| WO | WO-2019006380 A2 | 1/2019 | | |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al, "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al, "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

FIG. 2

TAPERED PROSTHETIC HEART VALVES WITH VALVULAR STRUCTURES FORMING TAPERED FLOW CHANNELS

CROSS-REFERENCE TO RELATED APPLICATIONS

This application is a continuation of PCT Application No. PCT/US2021/049537, filed Sep. 8, 2021, which claims the benefit of U.S. Provisional Application No. 63/076,293, filed Sep. 9, 2020, all of which are incorporated by reference herein.

FIELD

The present disclosure relates to prosthetic heart valves, in particular, tapered prosthetic heart valves that have valvular structures forming tapered flow channels.

BACKGROUND

The human heart can suffer from various valvular diseases, which can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped configuration on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Such expandable, transcatheter heart valves have an annular metal frame and prosthetic leaflets supported within the frame. In general, these leaflets can be designed to form a tubular flow channel during the systole phase of the cardiac cycle. At locations where the leaflets attach to the frame, tab portions of the leaflets can project radially inward to act as protective standoffs, which prevent the leaflets from contact with and damage from the frame during systole. The outlet cross-sectional area of the flow channel formed by the leaflets may thus be limited by the geometry of the flow channel as well as the inwardly-projecting leaflet tab portions.

Accordingly, a need exists for improved prosthetic heart valves and methods for securing leaflet assemblies to a frame of the prosthetic heart valve.

SUMMARY

In one aspect, a prosthetic heart valve comprises a frame and a valvular structure. The frame can be expandable between a crimped configuration and an expanded configuration. The valvular structure can comprise a plurality of leaflets. Each leaflet can have a pair of tabs. The tabs of the pair can be on opposite sides from each other with respect to a centerline of the leaflet. The valvular structure can have a plurality of commissure tab assemblies formed by paired tabs of adjacent leaflets. The valvular structure can be coupled to the frame via the plurality of commissure tab assemblies. The frame can have an inflow end and an outflow end separated from the inflow end along an axial direction of the frame. The inflow end of the frame can have a first diameter in the crimped configuration and a second diameter greater than the first diameter in the expanded configuration. The outflow end of the frame can have a third diameter in the crimped configuration and a fourth diameter greater than the third diameter in the expanded configuration. The frame in the expanded configuration can have an inverted frustoconical shape, with the fourth diameter of the outflow end being greater than the second diameter of the inflow end. A taper angle of the inverted frustoconical shape of the frame in the expanded configuration can be 6-8°. The frame in the expanded configuration can have a height along the axial direction from the inflow end to the outflow end. A ratio of the height of the frame in the expanded configuration to the second diameter of the inflow end can be 0.63-0.9. The valvular structure can be constructed to transition between a closed configuration, where the leaflets prevent blood flow from the inflow end to the outflow end of the frame, and an open configuration, where the leaflets deflect away from a central axis of the frame to form a flow channel from the inflow end to the outflow end of the frame. The flow channel formed by the valvular structure in the open configuration can be tapered such that a cross-sectional area at an outlet of the flow channel is greater than a cross-sectional area at an inlet of the flow channel.

In another aspect, a prosthetic heart valve comprises a frame and a valvular structure. The frame can be expandable between a crimped configuration and an expanded configuration. The valvular structure can comprise a plurality of leaflets. Each leaflet can have a pair of tabs and an upper free edge portion extending between the tabs. The valvular structure can have a plurality of commissure tab assemblies formed by paired tabs of adjacent leaflets. The valvular structure can be coupled to the frame via the plurality of commissure tab assemblies. The frame can have an inflow end and an outflow end separated from the inflow end along an axial direction of the frame. The frame in the expanded configuration can have a first inverted frustoconical shape, with a first diameter at the outflow end that is greater than a second diameter at the inflow end. The valvular structure can be constructed to transition between a closed configuration, where the leaflets prevent blood flow from the inflow end to the outflow end of the frame, and an open configuration, where the leaflets form a flow channel from the inflow end to the outflow end of the frame. In transitioning between the open configuration and the closed configuration, each leaflet can bend about a respective bending axis at each tab. Each bending axis can be disposed at or substantially adjacent to a radially-inner circumferential surface of the frame where the valvular structure is coupled via the respective commissure tab assembly. The flow channel formed by the valvular structure in the open configuration can adopt a second inverted frustoconical shape, with a cross-sectional area at an outlet of the flow channel that is greater than a cross-sectional area at an inlet of the flow channel. The second inverted frustoconical shape can have a sidewall extending between the inlet and the outlet of the flow channel that is substantially parallel to a facing sidewall of the first inverted frustoconical shape between the inflow and outflow ends of the frame. The prosthetic heart valve can be constructed such that blood flow through the flow channel of the valvular structure in the open configuration produces an annular back flow region adjacent to a radially-inner circumferential surface of the frame. The commissure tab assemblies can be positioned at respective locations along the axial direction within the annular back flow region such that the back flow urges the upper free edge portions of the leaflets from contacting the frame when blood flows through the flow channel of the valvular structure in the open configuration.

In another aspect, an assembly for implanting a prosthetic heart valve in a patient's body can comprise a delivery apparatus and the prosthetic heart valve of any of the above noted aspects. The delivery apparatus can comprise an elongated shaft. The prosthetic heart valve can be mounted on the elongated shaft in a crimped configuration for delivery into the patient's body.

In another aspect, a method of implanting a prosthetic heart valve in a patient's body can comprise inserting a distal end of a delivery apparatus into vasculature of a patient. The delivery apparatus can comprise an elongated shaft. The prosthetic heart valve can be any of the above noted aspects and can be releasably mounted in the crimped configuration on the elongated shaft of the delivery apparatus. The method can further comprise advancing the prosthetic heart valve to a desired implantation site, and using the delivery apparatus to radially expand the prosthetic heart valve to the expanded configuration, thereby implanting the prosthetic heart valve at the desired implantation site.

In another aspect, a method of assembling a prosthetic heart valve can comprise forming a plurality of tab assemblies with a plurality of leaflets. Each leaflet can have two tabs arranged on opposite sides of a body of the leaflet. Each commissure tab assembly can include a pair of tabs from adjacent leaflets. The method can further comprise coupling each commissure tab assembly, either directly or via a coupling member, to a respective portion of a valve frame. The valve frame can have an inverted frustoconical shape, with a first diameter at a first end being greater than a second diameter at an opposite second end. A taper angle of the inverted frustoconical shape of the valve frame can be 6-8°. The valve frame can have an end-to-end height that is less than the second diameter. A ratio of the end-to-end height of the valve frame to the second diameter can be 0.63-0.9. The commissure tab assemblies can be coupled to the respective portions of the valve frame at axial locations where, when the prosthetic heart valve is implanted, an annular back flow region is generated during systole by blood flowing through a flow channel formed by the leaflets. The annular back flow region can be adjacent to a radially-inner circumferential surface of the valve frame.

Any of the various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

BRIEF DESCRIPTION OF THE DRAWINGS

FIG. 2 is a perspective view of an exemplary tapered frame of the prosthetic heart valve of FIG. 1.

DETAILED DESCRIPTION

Figure 1:
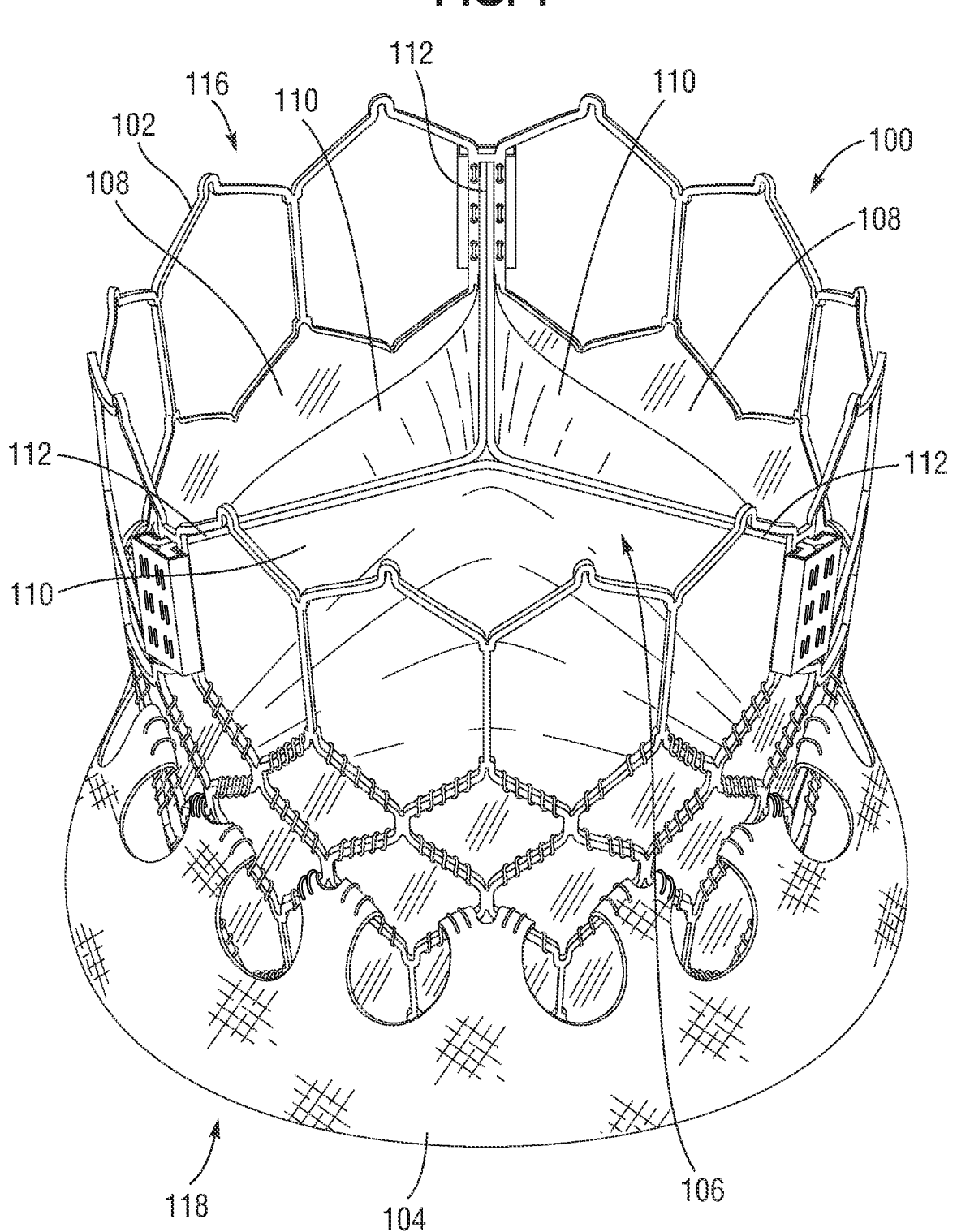
FIG. 1 is a perspective view of an exemplary prosthetic heart valve having a tapered frame.

The subject matter is described with exemplary implementations and examples. In some cases, as will be recognized by one skilled in the art, the disclosed implementations and examples may be practiced without one or more of the disclosed specific details, or may be practiced with other methods, structures, and materials not specifically disclosed herein. All the implementations and examples described herein and shown in the drawings may be combined without any restrictions to form any number of combinations, unless the context clearly dictates otherwise, such as if the proposed combination involves elements that are incompatible or mutually exclusive. The sequential order of the acts in any process described herein may be rearranged, unless the context clearly dictates otherwise, such as if one act requires the result of another act as input.

For the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein with reference to the prosthetic heart valve assembly and implantation and structures of the prosthetic heart valve, "proximal" refers to a position, direction, or portion of a component that is closer to the user and a handle of the delivery system or apparatus that is outside the patient, while "distal" refers to a position, direction, or portion of a component that is further away from the user and the handle, and closer to the implantation site. The terms "longitudinal" and "axial" refer to an axis extending in the proximal and distal directions, unless otherwise expressly defined.

The terms "axial direction," "radial direction," and "circumferential direction" have been used herein to describe the arrangement and assembly of components relative to the geometry of the frame of the prosthetic heart valve. Such terms have been used for convenient description, but the disclosed subject matter is not strictly limited to the description. In particular, where a component or action is described relative to a particular direction, directions parallel to the specified direction as well as minor deviations therefrom are included. Thus, a description of a component extending along an axial direction of the frame does not require the component to be aligned with a center of the frame; rather, the component can extend substantially along a direction parallel to a central axis of the frame.

As used herein and in the claims, the terms "integrally formed" and "unitary construction" refer to a construction that does not include any welds, fasteners, or other means for securing separately formed pieces of material to each other.

As used herein and in the claims, operations that occur "simultaneously" or "concurrently" occur generally at the same time as one another, although delays in the occurrence of operation relative to the other due to, for example, spacing between components, are expressly within the scope of the above terms, absent specific contrary language.

As used herein and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language. The term "and/or" means "and" or "or," as well as "and" and "or."

As used herein and in the claims, the term "in a range of" or "in a range within" or "in a range from" includes the end points of the range, unless stated otherwise.

Directions and other relative references may be used to facilitate discussion of the drawings and principles herein, but are not intended to be limiting. For example, certain terms may be used such as "inner," "outer," "upper," "lower," "inside," "outside,", "top," "bottom," "interior," "exterior," "left," right," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over. Nevertheless, it is still the same part and the object remains the same.

Described herein are prosthetic heart valves that have tapered geometries. In some implementations, a prosthetic heart valve includes a tapered frame that gradually expands in diameter from the inflow end thereof to the outflow end thereof. The prosthetic heart valve further includes a valvular structure coupled to the frame via respective commissure tab assemblies. When in an open configuration, the valvular structure forms a tapered flow channel, which may follow a similar profile as the tapered frame. For example, the tapered flow channel can have a cross-sectional area that gradually increases from an inlet of the flow channel to an outlet of the flow channel. The outlet of the flow channel can thus offer a larger cross-sectional area for blood to flow therethrough.

Figure 2:
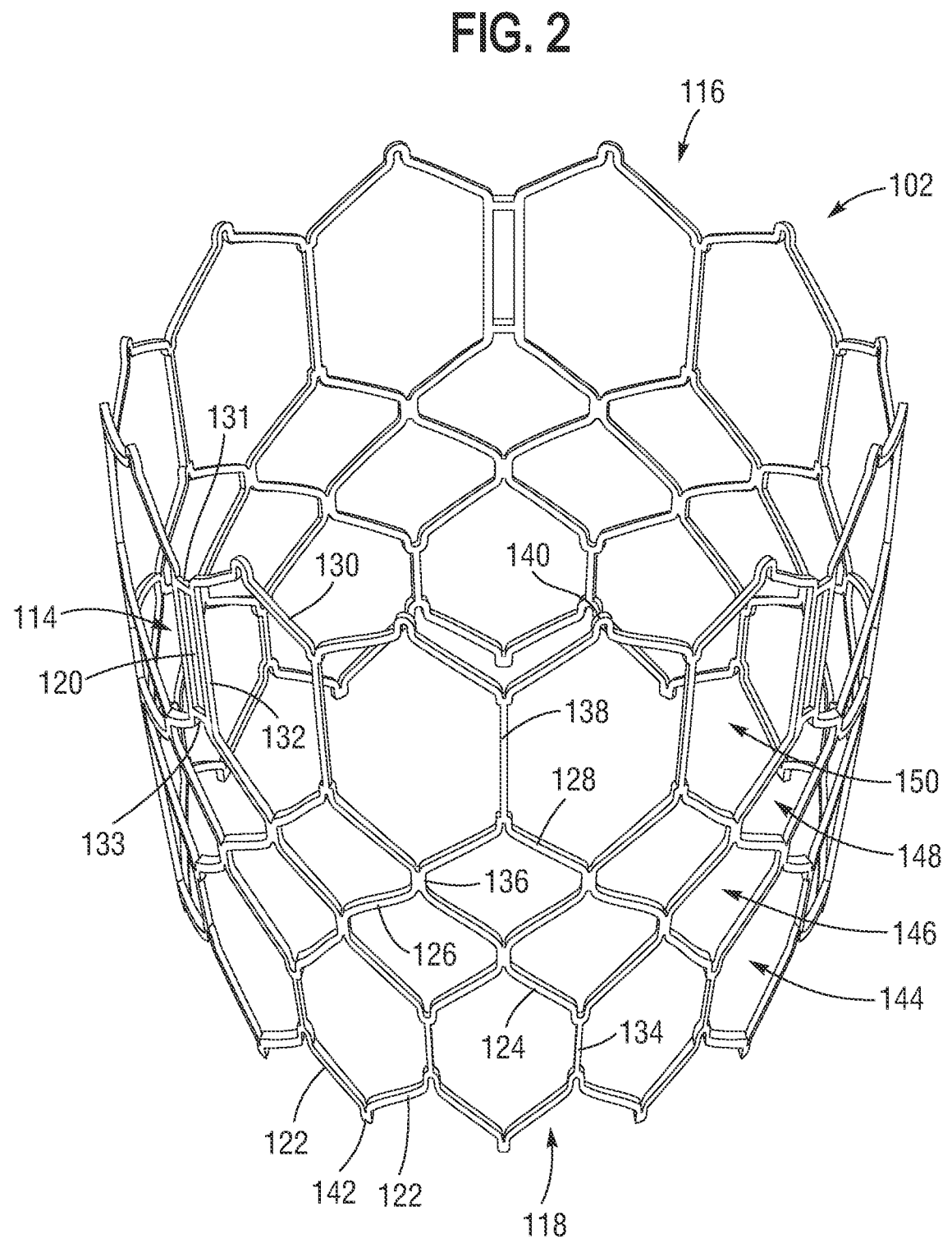

The tapered prosthetic heart valves disclosed herein can be radially compressible and expandable between a radially-compressed configuration (also referred to herein as a crimped configuration or crimped state) and a radially-expanded configuration (also referred to herein as a deployed configuration or deployed state). FIGS. 1-2 illustrate various features of an exemplary prosthetic heart valve 100. The tapered prosthetic heart valve 100 can be crimped on or retained by an implant delivery apparatus in the radially-compressed configuration while the prosthetic heart valve is routed through the anatomy of a patient to the patient's heart, and then expanded to the radially-expanded configuration once the tapered prosthetic heart valve reaches a desired implantation site within the heart. In particular examples, the prosthetic heart valve 100 can be implanted within the native aortic annulus, although it also can be implanted at other locations in the heart, including within the native mitral valve (e.g., mitral valve 260 in FIGS. 10A-10E), the native pulmonary valve (e.g., pulmonary valve 258 in FIGS. 10A-10E), or the native tricuspid valve (e.g., tricuspid valve 256 in FIGS. 10A-10E). The tapered prosthetic heart valves disclosed herein may be used with a variety of implant delivery apparatuses, and examples thereof are discussed in further detail below.

The prosthetic heart valve 100 can include a tapered frame 102 (also referred to herein as a tapered stent). The frame 102 can have a first axial end 116 and a second axial end 118. In the depicted example, the first axial end 116 can be an outflow end, and the second axial end 118 can be an inflow end. The diameter of the tapered frame 102 can expand from inflow end 118 to outflow end 116 of the frame 102, such that the diameter at the outflow end 116 is greater than the diameter at the inflow end 118. In some implementations, the expansion of the diameter of the tapered frame 102 can be gradual or linear, e.g., such that the tapered frame 102 adopts an inverted frustoconical shape in the expanded configuration. In some implementations, the tapered frame 102 can be constructed such that, in the crimped configuration, the diameter at the inflow end 118 is substantially the same as the diameter at the outflow end 116, for example, to assist in the crimping of the prosthetic heart valve 100 onto the delivery apparatus and/or navigation of the prosthetic heart valve 100 through the patient vasculature. Alternatively, in some implementations, the frame 102 can be constructed such that, in the crimped configuration, the frame retains a tapered shape, with the diameter at the outlet flow end 116 being greater than the diameter at the inflow end 118. In such implementations, the taper angle of the frame in the crimped configuration may be different than that of the frame in the expanded configuration.

In some implementations, the outflow end 116 can be coupled to the delivery apparatus for delivery and implantation of the tapered prosthetic heart valve 100 within the native aortic valve using a transfemoral, retrograde delivery approach. Thus, in the delivery configuration of the prosthetic heart valve 100, the outflow end 116 can be considered the proximal-most end of the prosthetic heart valve 100. In other embodiments, the inflow end 118 can instead be coupled to the delivery apparatus, depending on the particular native valve being replaced and the delivery technique that is used (e.g., trans-septal, transapical, etc.). For example, the inflow end 118 can be coupled to the delivery apparatus (and therefore would be the proximal-most end of the prosthetic heart valve in the delivery configuration) when delivering the prosthetic heart valve to the native mitral valve via a trans-septal delivery approach.

In some implementations, the frame 102, or components thereof (e.g., struts), can be made of any of various suitable plastically-expandable materials or self-expanding materials, as known in the art. Plastically-expandable materials that can be used to form the frame 102 can include, but are not limited to, stainless steel, biocompatible high-strength alloys (e.g., a cobalt-chromium or a nickel-cobalt-chromium alloys), polymers, or combinations thereof. In particular examples, frame 102 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. Self-expanding materials that can be used to form the frame 102 can include, but are not limited to, nickel titanium alloy (NiTi), such as nitinol.

When constructed of a plastically-expandable material, the frame 102 (and thus the tapered prosthetic heart valve 100) can be crimped to the radially-compressed configuration on a delivery catheter and then expanded inside a patient by an inflatable balloon or equivalent expansion mechanism. Alternatively, when constructed of a self-expanding material, the frame 102 (and thus the prosthetic heart valve 100) can be crimped to the radially-compressed configuration and restrained in the compressed configuration by insertion into a sheath or equivalent mechanism of a delivery catheter. Once advanced to the desired implantation site, the prosthetic heart valve can be advanced from the delivery sheath, thereby allowing the prosthetic heart valve to expand to its functional size.

In some implementations, struts of the frame 102 are pivotable or bendable relative to each other to permit radial expansion and contraction of the frame 102. For example, the frame 102 can be formed (e.g., via laser cutting, electroforming or physical vapor deposition) from a single piece of material (e.g., a metal tube). As best seen in FIG. 2, the frame 102 can be formed with a plurality of circumferentially-spaced commissure windows 114. A valvular structure 106 can be coupled to the frame 102 at the commissure windows 114. For example, the valvular structure 106 can have a plurality of commissure tab assemblies 112, each corresponding to a respective one of the commissure windows 114 of the frame 102. As described in further detail below with respect to FIGS. 4A-4B, the commissure tab assemblies 112 can be inserted through and attached to the respective commissure windows 114.

In some implementations, the commissure windows 114 can be disposed at equal intervals along the circumferential direction of the frame 102. In the illustrated example of FIG. 1, the valvular structure 106 comprises three leaflets 110 (e.g., a tricuspid structure), and the commissure windows 114 are equally spaced at 120° intervals (i.e., 0°, 120°, and 240°) along the circumference of the frame 102. However, other spacings and numbers of commissure windows 114 are also possible according to one or more contemplated embodiments. For example, in some implementations, the valvular structure 106 comprises two leaflets 110 (e.g., a bicuspid structure), and the commissure windows 114 are disposed on opposite sides of the frame (e.g., aligned on a same diameter of the frame). Multiple support struts 138 can be disposed along the circumference of the frame between the pair of commissure windows 114.

As shown in FIG. 2, each commissure window 114 can be formed within or part of a lattice structure formed by axial struts and angled struts. At the inflow end 118 of the frame 102, pairs of angled struts 122 (e.g., connecting together at ends 142) are respectively connected to pairs of angled struts 124 by respective axial struts 134, thereby forming a circumferentially-extending row of open cells 144 adjacent to the inflow end 118. A second circumferentially-extending row of open cells 146 can be formed by the pairs of angled struts 124 connected at respective ends thereof to respective ends of pairs of angled struts 126 (e.g., connecting together at joint or union 136). A third circumferentially-extending row of open cells 148 can be formed by the pairs of angled struts 126 connected by joints 136 to respective ends of pairs of angled struts 128. At the outflow end 116 of the frame 102, the pairs of angled struts 128 are respectively connected to pairs of angled struts 130 (e.g., connecting together at ends 140) by either respective axial struts 138 or commissure windows 114, thereby forming a fourth circumferentially-extending row of open cells 150 adjacent to the outflow end 116. In some implementations, an open area of each cell 150 can be greater than the open area of each cell 144, 146, and/or 148.

In the illustrated example of FIG. 2, each commissure window 114 can have a rectangular construction, with a central opening 120 defined by a pair of side struts 132 (e.g., extending primarily along an axial direction of the frame 102), a top cross-bar 131 (e.g., extending primarily along a circumferential direction of the frame 102), and a bottom cross-bar 133 (e.g., extending primarily along the circumferential direction of the frame 102). Each window strut 132 can connect to (e.g., by joining or integrally formed with) an adjacent angled strut 130 at a first end of strut 132 (e.g., closest to the outflow end 116 of the frame 102) and can connect to (e.g., by joining or integrally formed with) an adjacent angled strut 128 at a second end of strut 132 (e.g., closets to the inflow end 118 of the frame 102). Other shapes and configurations for commissure window 114 are also possible according to one or more contemplated embodiments. For example, instead of a rectangular opening 120, the commissure window can define a an opening that is square, oval, square-oval, triangular, L-shaped, T-shaped, C-shaped, or any other shape. Alternatively or additionally, instead of being closed at axial ends as in window 114, one or both axial ends of the window 114 can be open, for example, by eliminating cross-bar 131, eliminated cross-bar 133, and/or repositioning one or both cross-bars 131, 133 (e.g., to form an H-shaped commissure window). In such window configurations, commissure tab assemblies can be inserted axially into the opening of the window instead of, or combination with, insertion along the radial direction of the frame.

As shown in FIG. 1, the tapered prosthetic heart valve 100 can also include one or more skirts or sealing members. For example, the tapered prosthetic heart valve 100 can include an inner skirt 108 mounted on an interior of the frame 102 (e.g., radially-inward of a frustoconical wall formed by the lattice structure of the struts of the frame) and/or an outer skirt 104 mounted on an exterior of the frame 102 (e.g., radially-outward of the frustoconical wall formed by the lattice structure of the struts of the frame). The inner skirt 108 can be a circumferential inner skirt that spans an entire circumference of the interior of the frame 102. The inner skirt 108 can function as a sealing member to prevent, or at least reduce, perivalvular leakage (e.g., when the valve is placed at the implantation site) and as an attachment surface to anchor a portion of the leaflets 110 to the frame 102. For example, the cusp edge portions 158 of the leaflets 110 (see FIG. 3A) can be attached to the inner skirt 108, which in turn can be attached to selected struts 124-128 of the frame 102. In some implementations, the leaflets 110 can have a rein-forcing member (e.g., fabric strip) at the cusp edge portion 158 where the leaflets 110 are attached to the inner skirt 108. The outer skirt 104 can function as a sealing member by sealing against the tissue of the native valve annulus and can help to reduce paravalvular leakage past the prosthetic heart valve 100.

The inner and outer skirts 108, 104 can be formed from any of various suitable biocompatible materials, including any of various synthetic materials (e.g., polyethylene tere-phthalate (PET)) or natural tissue (e.g., pericardial tissue). The inner and outer skirts 108, 104 can be coupled to the frame 102 using sutures, adhesive, welding, and/or other means for attaching the skirts to the frame. Further details regarding the inner and outer skirts, techniques for assem-bling the leaflets to the inner skirt, and techniques for assembling the skirts on the frame are disclosed in U.S. Patent Application Publication Nos. 2012/0123529, 2019/0192296, and 2019/0365530, and International Patent Application Nos. PCT/US2020/014701 and PCT/US2020/024559, each of which is incorporated herein by reference.

The valvular structure 106 of the tapered prosthetic heart valve 100 can be configured to allow blood flow through the frame 102 in only one direction, for example, to regulate the flow of blood through the prosthetic heart valve 100 from the inflow end 118 to the outflow end 116. The valvular structure 106 can include, for example, a leaflet assembly formed by a plurality of leaflets 110 (three leaflets illustrated in FIG. 1). The leaflets 110 can be made of a flexible material, such the leaflets 110 can transition between an open configuration, where blood flows through the valve 100 via a flow channel formed by the leaflets, and a closed configuration, where the leaflets occlude blood flow through the valve 100. The leaflets 110 of the valvular structure 106 can be made from in whole or part, biological materials, biocompatible syn-thetic materials, or other such materials. Suitable biological materials can include, for example, bovine pericardium (or pericardium from other sources).

Figure 3A:
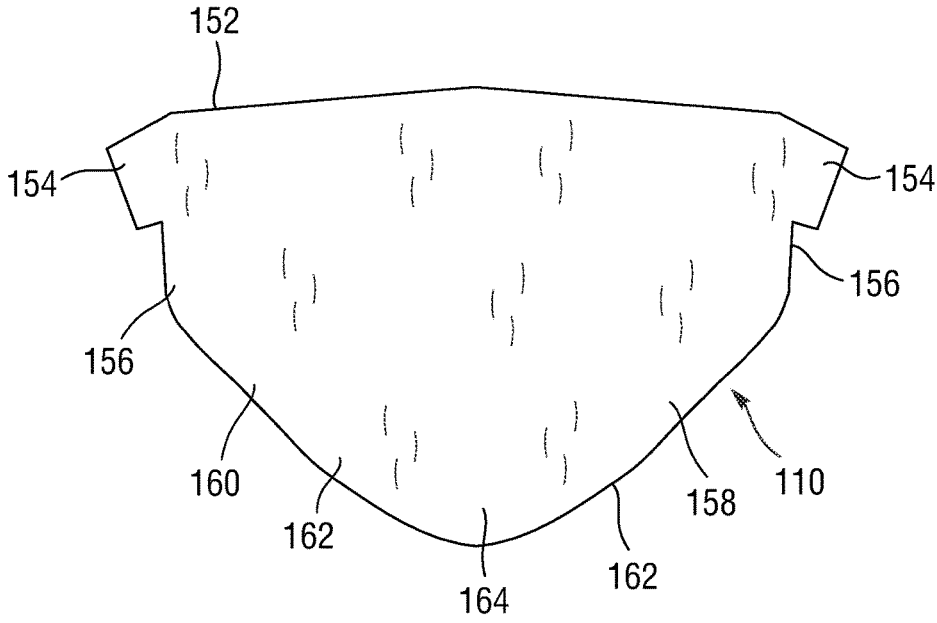
FIG. 3A is a plan view of an individual leaflet used to form the valvular structure of a prosthetic heart valve.

As shown in FIG. 3A, at an upper edge of the leaflet 110, an upper free edge portion 152 can extend between a pair of tabs 154 (also referred to herein as leaflet tabs or commis-sure tabs) on opposite ends of leaflet 110 with respect to centerline of the leaflet 110. As used here, "upper" and "lower" may be relative to a central longitudinal axis of the prosthetic heart valve 100 when the valvular structure is installed and coupled to frame 102, with upper being closer to the outflow end 116 of the valve 100 and lower being closer to the inflow end 118 of the valve 100. At the lower edge of the leaflet 110, a lower edge portion 158 (also referred to herein as a cusp edge portion) of the leaflet extending between respective ends of tabs 154 can include substantially-straight edge portions 156 and a substantially V-shaped intermediate edge portion 160. The substantially-straight edge portions 156 can extend downwardly from corresponding lower tabs 154 to connect to the substantially V-shaped intermediate edge portion 160 at opposite ends thereof. The substantially V-shaped intermediate edge por-tion 160 can have a smooth, curved apex portion 164 at a lower end of the leaflet 110 and a pair of oblique portions

162 that extend between respective edge portions 156 and the apex portion 164. The oblique portions 162 can have a greater radius of curvature than the apex portion 164. In some implementations, each leaflet 110 can have a reinforc-ing strip attached (e.g., via sewing) to the lower edge portion 158.

In the closed configuration (see FIGS. 5A-5B), upper free edge portions 152 of the leaflets 110 can come together to substantially occlude a cross-section of the frame 102, thereby blocking a flow path within the prosthetic heart valve 100 between the inflow end 118 and the outflow end 116. In the open configuration (see FIGS. 6A-6B), upper free edge portions 152 of the leaflets 110 can deflect away from a central axis of the prosthetic heart valve 100 and toward the surrounding frame 102, thereby forming a flow channel by which blood can flow from the inflow end 118 to the outflow end 116 of the prosthetic heart valve 100. In transitioning between the open and closed configurations, each leaflet 110 can bend at locations defined, at least in part, by attachment points to the frame 102. For example, tabs of adjacent leaflets 110 can be arranged together to form commissure tab assemblies 112 that are coupled (directly or indirectly) to respective commissure windows 114 of the frame 102, thereby securing at least a portion of the valvular structure 106 to the frame 102. As described in further detail below, the construction and attachment of the commissure tab assemblies 112 can be such that respective bending axes for the leaflets 110 are at or substantially adjacent to a radially-inner surface of the frame 102. In some implemen-tations, such arrangement of the leaflet bending axes can help maximize an outlet cross-sectional area of the flow channel formed by the valvular structure 106 in the open configuration.

In some implementations, the valvular structure 106 is constructed and/or coupled to the frame 102 such that, in the open configuration, the leaflets 110 form a tapered flow channel between the inflow end 118 and the outflow end 116 of the prosthetic heart valve 100. A cross-sectional area of the tapered flow channel can expand from an inlet of the flow channel (closest to the inflow end 118 of the frame 102) to an outlet of the flow channel (closest to the outlet end 116 of the frame 102), such that the cross-sectional area at the flow channel outlet is greater than the cross-sectional area at the flow channel inlet. In some implementations, tapered flow channel formed by the leaflets 110 in the open con-figuration can have a similar profile as the tapered frame 102. For example, the expansion of the cross-sectional area of the flow channel can be gradual or linear, e.g., such that the flow channel formed by the leaflets 110 adopts an inverted frustoconical shape in the open configuration.

In some implementations, the tapered geometry of the flow channel formed by the leaflets 110 in the open con-figuration can be a product of the coupling to frame 102, shapes, and/or arrangements of the tabs 154 and/or the lower edge portions 158 of the leaflet 110. For example, in some implementations, a shape of the leaflet 110 can be designed such that the commissure tabs 154 are angled relative to an axial direction of the frame 102. For example, as shown in FIG. 3A, an outermost edge (e.g., left or right edges) of each tab 154 can be arranged at a non-zero angle with respect to a centerline of the leaflet 110. Moreover, the top edge of each tab 154, can be arranged at a non-zero angle with respect to upper free edge portion 152, and the lower edge of each tab 154 can be arranged at a non-zero angle with respect to vertical edge portion 156. Since the top and bottom edges of each tab 154 are substantially perpendicular to the outermost edge of the tab 154, their respective arrangements may be a function of the non-zero angle (e.g., a first angle) selected for the outermost edge of each tab 154 with respect to the leaflet centerline. In some implementations, this first angle for each tab 154 can be selected to be the same as, or substantially the same as, a draft angle θ of the frame 102 (see FIG. 6C) of the prosthetic heart valve 100.

Figure 3B:
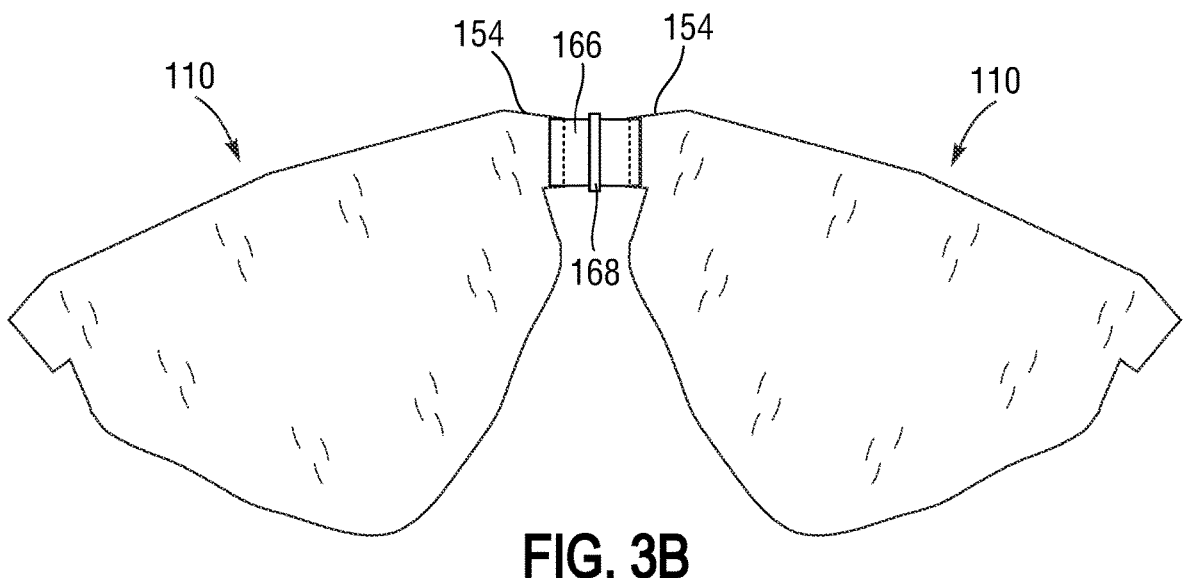
FIG. 3B illustrates an exemplary coupling between adjacent leaflets of the valvular structure using an exemplary flexible member.

The leaflets 110 can be secured to one another at their adjacent tabs 154 to form commissure tab assemblies 112 of the valvular structure 106. In some implementations, a plurality of coupling members 166 (one of which is shown in FIG. 3B) can be used to interconnect pairs of adjacent tabs 154 and to mount the leaflets 110 to the commissure window 114. For example, the coupling members 166 can be made from a flexible piece of woven PET fabric, although other synthetic and/or natural materials can be used. Each coupling member 166 can include a wedge 168 extending from the lower edge to the upper edge at the center of the coupling member. The wedge 168 can comprise be formed from a relatively thick, multi-filament or monofilament suture, yarn or cable (e.g., a braided, polyester suture, such as an Ethibond suture), a piece of cloth or fabric folded one or more times to increase its thickness, or any other structure. The wedge 168 can be attached to the coupling member 166, for example, via one or more sutures, adhesive, welding, or the like. As shown in FIG. 3B, the adjacent tabs 154 of a pair of leaflets 110 are in an overlapping relationship with opposite ends of the coupling member 166, with the wedge 168 centered between the tabs 154. Each tab 154 can be secured to a corresponding end portion of the coupling member 166, for example, via one or more sutures (e.g., sutures 172 in FIG. 4A), adhesive, welding, or the like.

Figure 4A:
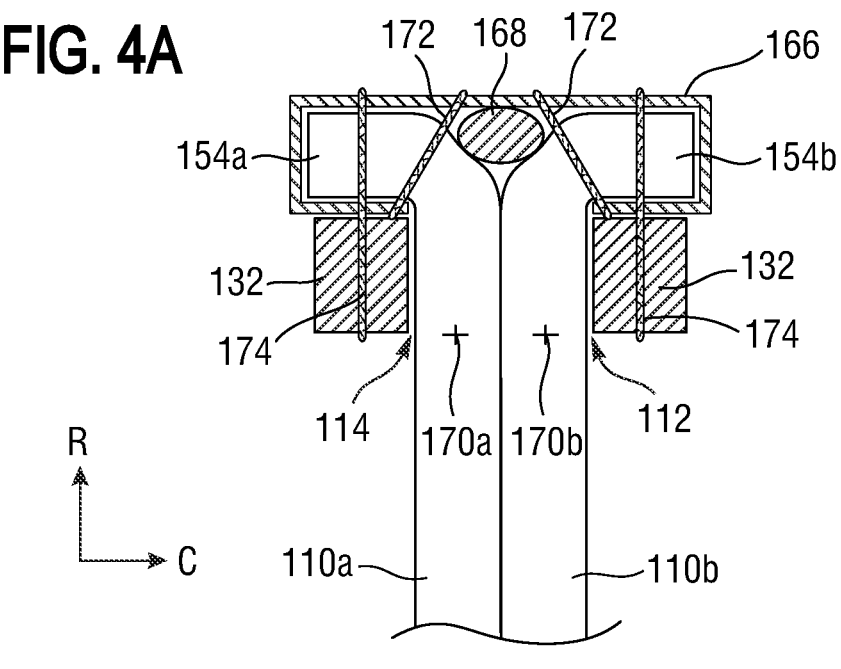
FIGS. 4A-4B are simplified cross-sectional and perspective views, respectively, showing an exemplary assembly of leaflets to the prosthetic heart valve frame of FIG. 2.
Figure 4B:
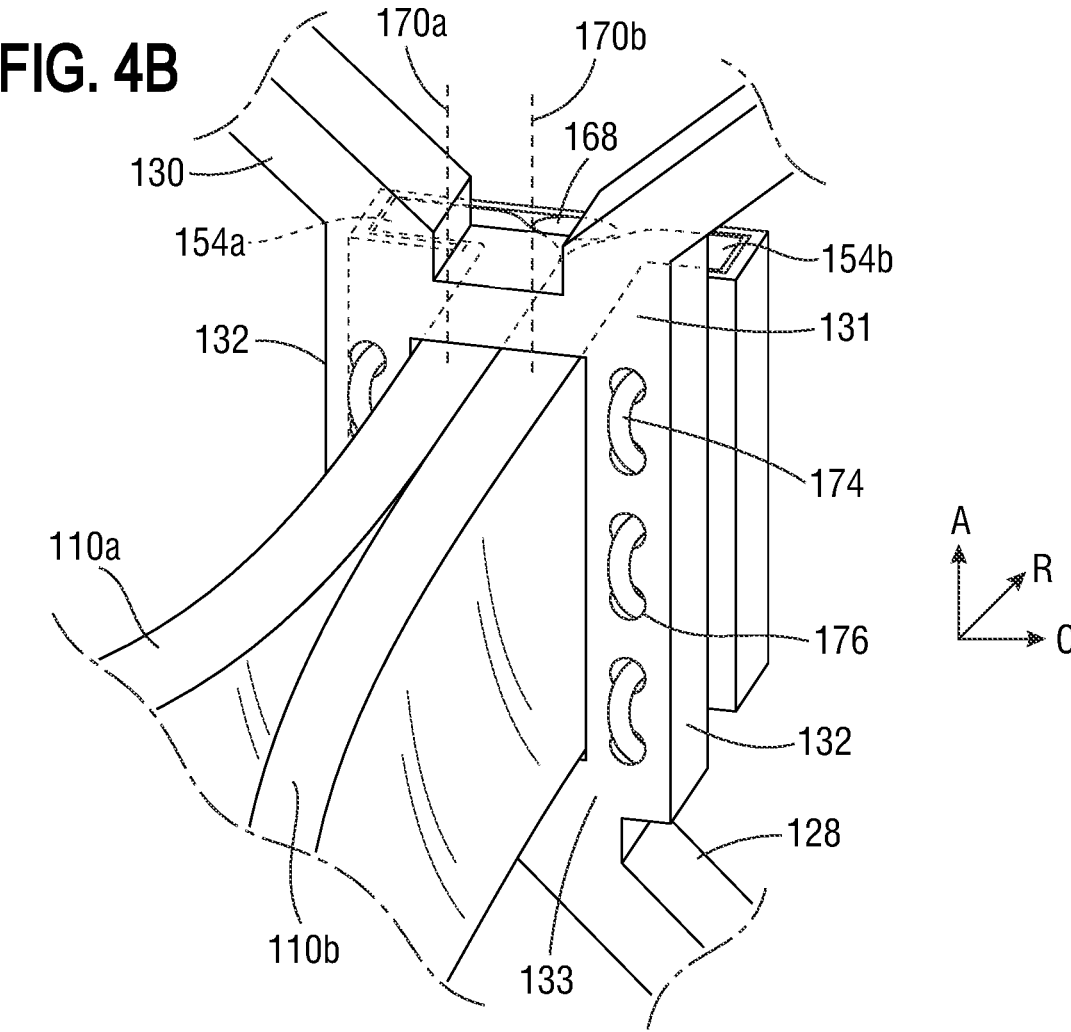

Each commissure tab assembly 112 of the valvular structure 106 can be inserted into the window opening 120 of a respective commissure window 114 and coupled thereto. For example, FIGS. 4A-4B show a top-down cross-sectional view and a simplified perspective view, respectfully, of an exemplary mounting configuration of a commissure tab assembly 112 to window 114 of the frame 102. For example, the commissure tab assembly 112, which is comprised of adjacent tabs 154a, 154b, coupling member 166, and wedge 168, can be folded in half such that leaflets 110a, 110b extend radially inward from the commissure tab assembly 112. The commissure tab assembly 112 can then be inserted through the window opening 120 (by advancing along a radial direction from a radially-inner end of the window 114 to a radially-outer end of the window 114), such that the tabs 154a, 154b, coupling member 166, and wedge 168 are disposed on a radially-outer side of the frame 102. The commissure tab assembly 112 can then be pressed radially inward at the wedge 168 such that one tab 154a and a portion of the coupling member 166 is folded against the window strut 132 on one side of the commissure window 114 and the other tab 154b and another portion of the coupling member 166 is folded against the window strut 132 on an opposite side of the commissure window 114. The commissure tab assembly 112 may thus form T-shape extending through window 114, with a first portion of each tab 154a, 154b extending along a circumferential direction, C, of the frame 102 and contacts the coupling member 166, and a second portion of each tab 154a, 154b extending along a radial direction, R, of the frame 102, contacting the corresponding second portion of the other tab 154b, 154a of the pair, and connecting the first portion to a central portion of the leaflet 110.

The commissure tab assembly 112 inserted into window opening 120 can then be mounted to the window 114 using one or more sutures. For example, sutures 174 can pass through respective holes 176 in the window struts 132 and through the respective portions of the commissure tab assembly 112 to secure the leaflets 110 to the frame 102. The commissure window 114, coupling member 166, and tabs 154 can be arranged such that each suture 174 passes through, in order from a radially-outer side to a radially-inner side, a first portion of the coupling member 166, the tab 154, a second portion of the coupling member 166, and the window strut 132. By utilizing the coupling member 166 to indirectly attach the commissure tabs 154 of the leaflets 110 to the frame 102, direct loading of the leaflets 110 and abrasion of the leaflets 110 (e.g., due to direct contact with the rigid surfaces of the struts 132) can be avoided or at least reduced.

Alternatively, in some implementations, tabs 154 without a coupling member can initially be inserted through the window opening 120 (by advancing along a radial direction from a radially-inner end of the window 114 to a radially-outer end of the window 114), after which the coupling member 166 and/or wedge 168 can be attached thereto. For example, once inserted through the opening 120, tabs 154 can be splayed (e.g., by displacing away from each other along the circumferential direction, C, of the frame 102), and the coupling member 166 can be wrapped around the exposed surfaces of the tabs 154. The wedge 168 can be inserted between and in contact with the coupling member 166 and the splayed tabs 154, for example, by displacing the wedge 168 along the axial direction, A, of the frame 102. The commissure tab assembly comprised of the splayed tabs 154 and coupling member 166 can then be attached to the struts 132 of the commissure window 114 by one or more sutures 174, similar to that described above.

Configurations and methods for coupling the commissure tab assemblies 112 to the frame 102 other than those described above are also possible according to one or more contemplated embodiments. For example, the commissure tab assemblies 112 can be coupled to the frame 102 in a manner similar to that illustrated in FIG. 7 or FIG. 11D, which are described in further detail herein below. Additional details regarding transcatheter prosthetic heart valves, including construction of valvular structures and the manner in which valvular structures can coupled to the frame, which may be employed in any of the examples or embodiments disclosed herein, can be found, for example, in U.S. Provisional Application No. 62/959,723; U.S. Pat. Nos. 6,730,118; 7,393,360; 7,510,575; 7,993,394; and 8,652,202; and U.S. Patent Application Publication No. 2018/0325665, all of which are incorporated herein by reference in their entireties.

In some implementations, the commissure tab assemblies 112 are mounted to the frame 102 such that the points at which each leaflet 110 bend in transitioning between open and closed configurations are at or as close as possible to the frame 102. For example, as shown in FIGS. 4A-4B, leaflets 110a, 110b can bend about respective bending axes 170a, 170b in transitioning between the open and closed configurations. Each bending axis 170a, 170b can be substantially parallel to an axial direction, A, of the frame 102. By positioning the bending axes 170a, 170b at or substantially adjacent to the frame 102, a cross-sectional area at the outlet of the flow channel formed by the valvular structure 106 in the open configuration can be maximized, or at least increased. In such embodiments, the upper free edge portion 152 of each leaflet 110, and in particular the tabs 154 of each leaflet 110, may be considered to lack any attachment radially-inward of the frame 102 (e.g., attached only at portions of the leaflet that are at a radial distance from a center of the prosthetic heart valve 100 equal to or greater than a radial distance of the corresponding portion of the frame 102).

Figures 5A, 5B, 6A, 6B:
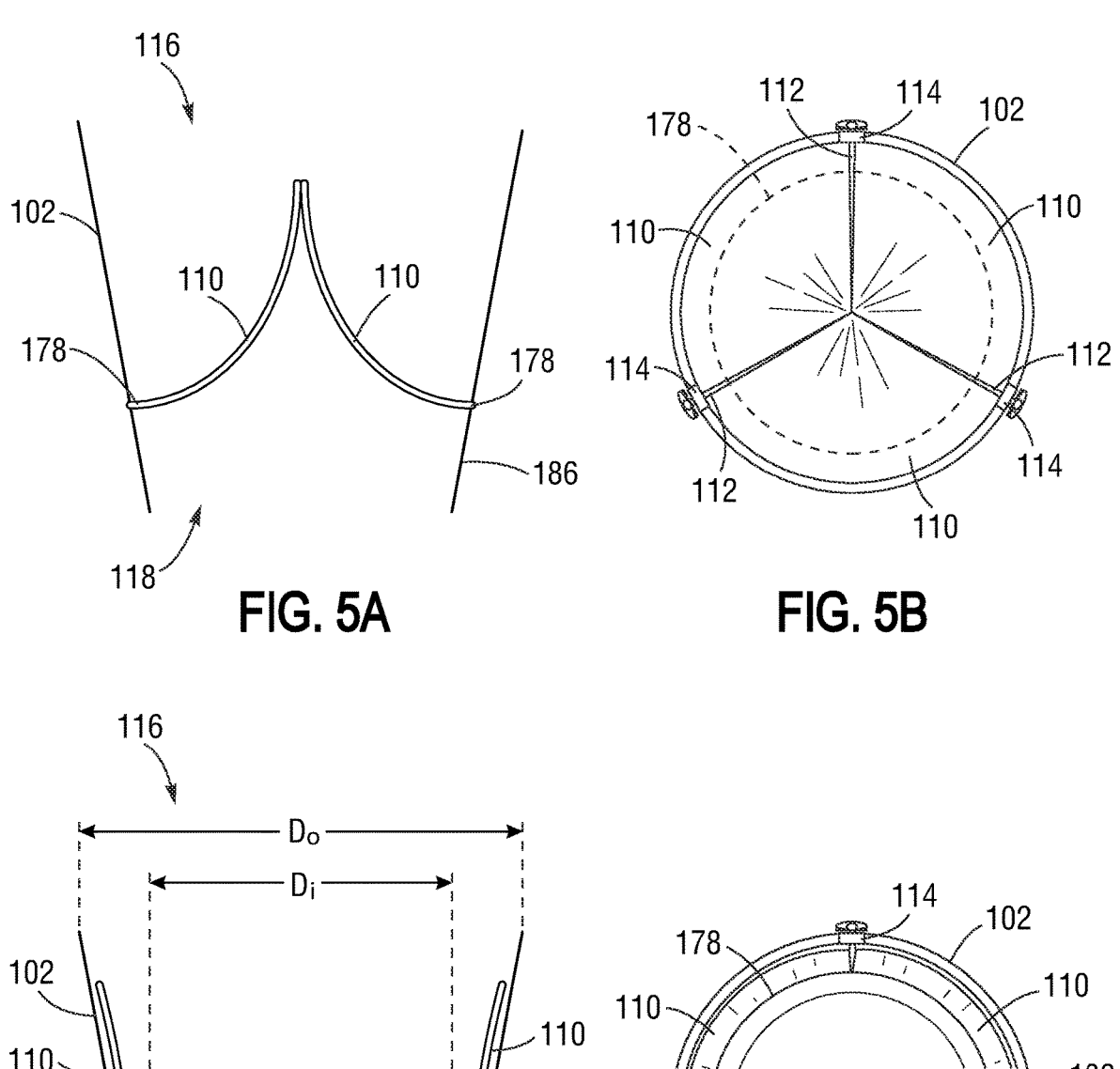
FIGS. 5A-5B are simplified cross-sectional and outflow end views, respectively, of the prosthetic heart valve of FIG. 1 when the valvular structure is in a closed configuration.
FIGS. 6A-6B are simplified cross-sectional and outflow end views, respectively, of the prosthetic heart valve of FIG. 1 when the valvular structure is in an open configuration.

While the positioning of the bending axes 170a, 170b at or substantially adjacent to the frame 102 can maximize a cross-sectional area of the flow channel outlet, it may also subject the leaflets 110 to damage due to contact with the surrounding portions of the frame 102. For example, simplified representations of an exemplary prosthetic heart valve 100 in a closed configuration and in an open configuration are shown in FIGS. 5A-5B and 6A-6B, respectively. The lower edge portion of each leaflet 110 can be coupled to the frame 102 at 178 (e.g., via inner skirt 108 attached to struts of the frame), which can define an inlet of the flow channel formed by the valvular structure in the open configuration. When the leaflets 110 transition to the open configuration (e.g., during systole), the upper free edge portions of the leaflets (e.g., proximal to the outflow end 116 of the frame) deflect away from a central axis of the prosthetic heart valve 100 and toward the surrounding frame 102 to form a tapered flow channel, as shown in FIGS. 6A-6B. The outlet of the tapered flow channel can be defined by upper free edge portions of the leaflets 110 and the commissure tab assemblies 112. In some implementations, the leaflets 110 in the open configuration can extend substantially parallel to adjacent sidewalls of the frame 102 (e.g., a sidewall extending formed between the inlet and outlet of the flow channel is substantially parallel to a facing sidewall of the inverted frustoconical shape formed by the frame). Alternatively, in some implementations, the flow channel formed by the leaflets 110 can have a taper angle that is less than the taper angle of the adjacent frame 102. In either case, the tapered flow channel formed by the leaflets 110 can have a similar geometry as the surrounding frame 102, for example, an inverted frustoconical shape.

In some implementations, the inlet of the flow channel can be spaced along the axial direction of the frame 102 from the inflow end 118 of the frame 102, thereby defining an initial tapered entry portion 186 formed by the frame 102 prior to the flow channel formed by the leaflets 110. In some implementations, the inner skirt 108 and/or the outer skirt 104 forms an impermeable barrier over entry portion 186, and, in some implementations, the impermeable entry portion 186 may be considered part of the flow channel even though it is formed by the frame rather than the leaflet 110. Alternatively, or additionally, the entry portion 186 may be eliminated, or at least minimized, such that the inlet end of the flow channel formed by leaflets 110 is as close to the inflow end 118 of the frame 102 as possible.

Figure 6C:
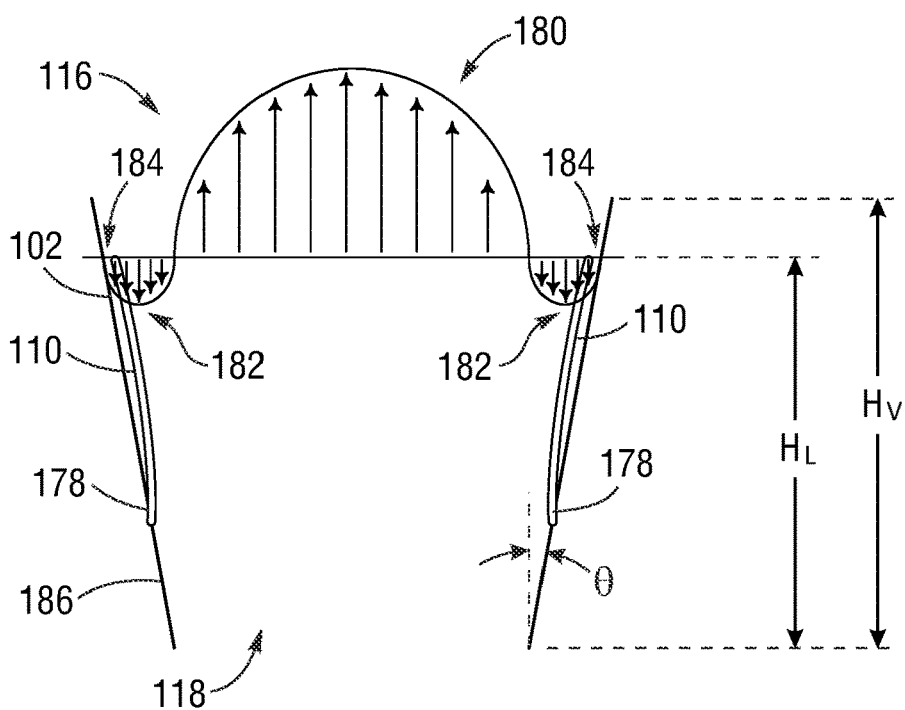
FIG. 6C is a simplified cross-sectional view showing certain fluid dynamic features of the prosthetic heart valve of FIG. 1 when the valvular structure is in an open configuration.
Figure 6D:
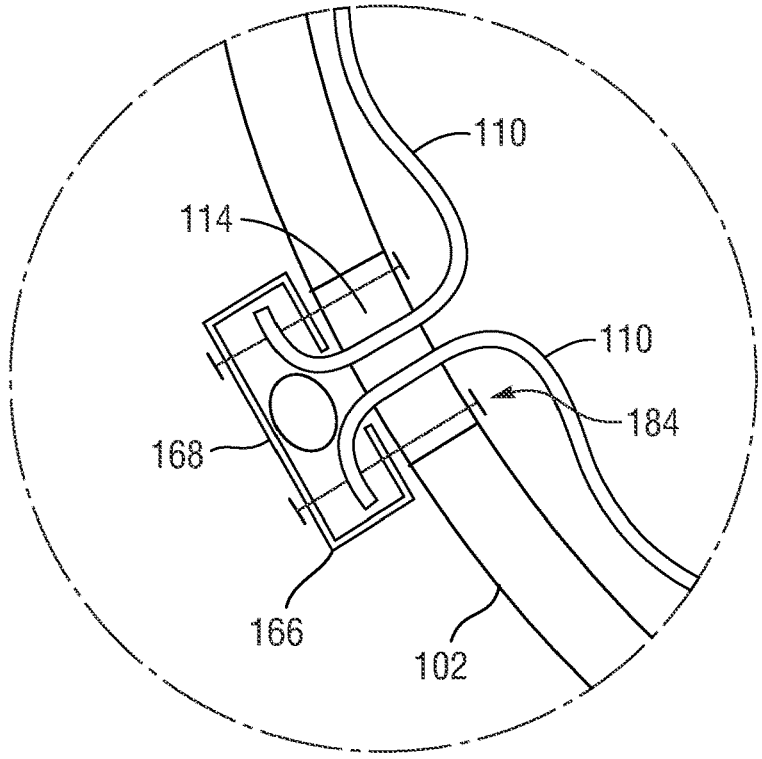
FIG. 6D is a detail view of leaflet attachment to the commissure window of the prosthetic heart valve of FIG. 1 when the valvular structure is in an open configuration.

Since there are no features that extend radially inward from the frame 102 in the vicinity of the upper free edge portions of the leaflets 110, the leaflets 110 would be susceptible to damage due to contact with the surrounding frame 102. However, in some implementations, the fluid dynamic effects of the tapered flow channel are employed to protect the leaflets 110 (or at least the upper free end portions of each leaflet) from contacting the frame 102 in the open configuration. For example, the tapered flow channel can generate flow separation within the flow channel formed by the leaflets 110. As shown in FIG. 6C, at an outlet of the flow channel formed by the leaflets 110, a velocity profile 180 (e.g., a Poiseuille flow profile) is thus formed by the fully developed blood flow in the channel, with the flow separation generating an annular back flow region 182 adjacent to an inner circumferential surface of the frame 102. Within the annular back flow region 182, the flow reverses direction (e.g., toward the inflow end 118 of the frame 102) as compared to a center of the flow channel (e.g., where the flow remains directed toward the outflow end 116 of the frame 102). Thus, when the valvular structure is in an open configuration (e.g., during systole), the back flow 182 can urge the upper free ends of the leaflets 110 away from contact with the frame 102 at 184 (FIGS. 6C-6D), thereby protecting the leaflets 110 from damage. The fluid dynamic effects of the tapered flow channel can thus obviate, or at least reduce, a need for inwardly-projecting tab portions or other inwardly-projecting features to protect the leaflets from contact with the frame.

In some implementations, the frame 102 and/or the flow channel formed by leaflets 110 can have a taper angle that is, for example, about 6-8°. As used herein, taper angle refers to the angle measured in a cross-sectional view between opposite walls of the frame or the flow channel. Thus, the taper angle may be considered to be double the value of draft angle θ illustrated in FIG. 6C. In some implementations, the frame in the expanded configuration can also have a low-profile (e.g., having an end-to-end height, $H_V$, along an axial direction between the inflow end 118 and the outflow end 116 that is less than a diameter, $D_i$, of the frame at the inflow end 118). For example, a ratio ($H_V/D_i$) of the height, $H_V$, of the frame to the diameter, $D_i$, at the inflow end can be about 0.63-0.9. Alternatively, or additionally, in some implementations, a ratio ($D_o/H_V$) of the diameter, $D_o$, of the frame 102 at the outflow end 116 to the height, $H_V$, of the frame can be less than about 1.75, for example, in a range of 1.2-1.73, inclusive. Using such low-profile frames with taper angles of about 6-8° can optimally position the commissure tab assemblies and/or upper free ends of the leaflets to take advantage of the protective features of the annular back flow region during systole.

In some implementations, the commissure tab assemblies of valvular structure can be mounted to other structures of the frame that allow the leaflet bending axes to be disposed at or substantially adjacent to the frame. For example, in some implementations, the valve frame may lack separate commissure windows integrated with the lattice structure formed by the struts of the frame. Instead, in such embodiments, each commissure tab assembly can be mounted to one of the open cells formed by the struts of the frame (e.g., open cells 150 adjacent to outflow end 116 of the tapered frame 102 in FIG. 2).

Figure 7:
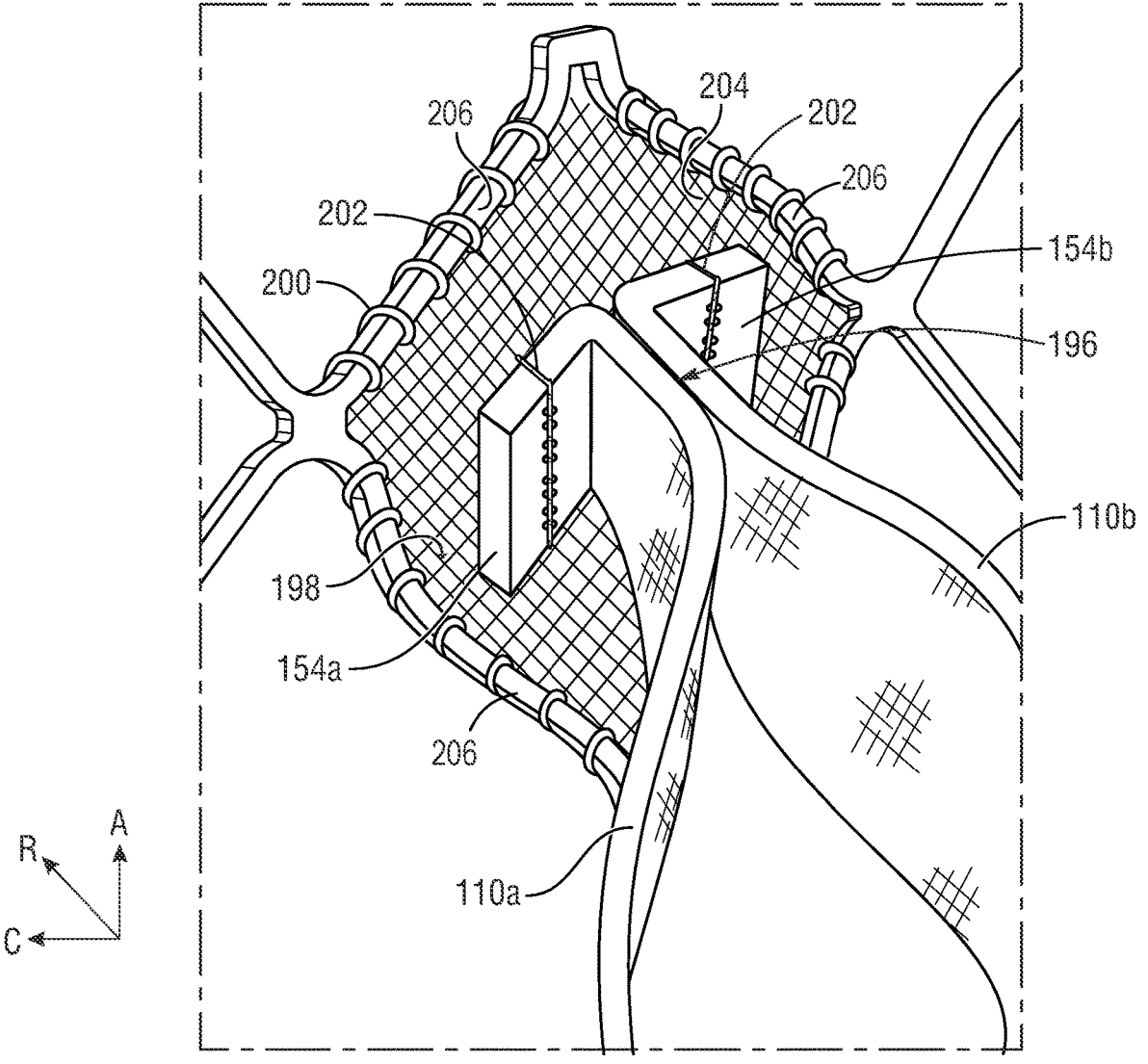
FIG. 7 is a detail, perspective view of another exemplary assembly of leaflets to prosthetic heart valve of FIG. 2.

For example, FIG. 7 illustrates an exemplary attachment of a commissure tab assembly 196 within an open cell 198, as viewed from a radially-inner side of the frame of a prosthetic heart valve. The open cell 198 can be formed by a plurality of interconnected struts 206 of the valve frame. A coupling member 204 can extend across the opening of the cell 198 and can be secured to the struts 206 forming the cell 198 by one or more sutures 200. For example, the coupling members 204 can be made from a flexible piece of woven PET fabric, although other synthetic and/or natural materials can be used. In the illustrated example of FIG. 7, the one or more sutures 200 extend through the coupling member 204 and loop around the frame struts 206, around a perimeter of the cell 198. The tabs 154a, 154b of adjacent leaflets 110a, 110b can be splayed in opposite directions along the circumferential direction to form a T-shape. The radially-outer surface formed by the splayed tabs 154a, 154b can contact the radially-inner face of the coupling member 204 and be coupled thereto, for example by one or more sutures 202. In some implementations, the tabs 154a, 154b can be coupled to the coupling member 204 prior to disposing the coupling member 204 within the open cell 198 and attaching to struts 206. Alternatively, in some implementations, the tabs 154a,

154*b* are attached to the coupling member 204 that is already attached to struts 206. In this way, the commissure tab assemblies can be mounted to the frame without requiring separate commissure windows. Further details regarding mounting of leaflet tabs to valve frames can be found in U.S. Provisional Application No. 63/024,951, U.S. Patent Application Publication No. 2020/0188099, and U.S. Pat. No. 9,393,110, all of which are incorporated herein by reference in their entireties.

As discussed above, the tapered prosthetic heart valves disclosed herein can be crimped on or retained by an implant delivery apparatus in the radially-compressed configuration while the prosthetic heart valve is routed through the anatomy of a patient to the patient's heart, and then expanded to the radially-expanded configuration once the tapered prosthetic heart valve reaches a desired implantation site within the heart. For example, referring to FIG. 8, a delivery apparatus 210 including a handle 212 can be used to deliver and implant prosthetic valve 100 in the following exemplary manner. The prosthetic valve 100 can be disposed on a distal end portion 216 of an elongated shaft of the delivery apparatus 210 in a radially-compressed configuration. The prosthetic valve 100 can be crimped on an inflatable balloon 214, or on another type of expansion member that can be used to radially expand the prosthetic valve 100. The distal end portion 216 of the delivery apparatus 210, including prosthetic valve 100, can be advanced through the vasculature to a selected implantation site (e.g., within a previously implanted host valve and/or within a native valve).

In the illustrated example, the distal end portion 216 of the delivery apparatus 210 and the prosthetic valve 100 are inserted into a femoral artery and advanced through the femoral artery and the aorta so as to position the prosthetic heart valve 100 within the native aortic valve 222 (or a host valve previously implanted within the native aortic valve 222). Although not specifically illustrated in FIG. 8, it should be appreciated that the distal end portion 216 of the delivery apparatus 210 can be advanced over a guidewire (e.g. similar to guidewire 229 in FIG. 10A), and that the delivery apparatus 210 can include an innermost shaft that defines a lumen for the guidewire, as is known in the art. The prosthetic valve 100 can then be deployed at the implantation site, such as by inflating the balloon 214. Further details of delivery apparatuses that can be used to deliver and implant plastically-expandable prosthetic heart valves, such as the prosthetic valve 100 (or any other of the prosthetic heart valves disclosed herein), are disclosed in U.S. Patent Application Publication Nos. 2017/0065415, 2016/0158497, and 2013/0030519, which are incorporated herein by reference. When the frame of the prosthetic valve is formed from a plastically-expandable material and expanded with a balloon or equivalent expansion mechanism, the tapered shape of the prosthetic valve can be achieved with a tapered balloon or a balloon otherwise shaped to expand the outflow end of the prosthetic valve to a greater extent than the inflow end of the prosthetic valve. In other embodiments, the prosthetic valve can have an expansion limiter to limit the extent that the inflow end of the prosthetic valve can be expanded. For example, the expansion limiter can be a belt or ring placed around the frame at or adjacent the inflow end. When the balloon is inflated to deploy the prosthetic valve, the balloon can expand the outflow end to a greater extent than the inflow end due to the presence of the belt or ring. Examples of expansion limiters that can be incorporated into the prosthetic valve are disclosed in U.S. Provisional Application No. 62/945,059, filed Dec. 6, 2019, and U.S. Patent Application Publication No. 2010/0256723, which are incorporated herein by reference.

If the prosthetic valve 100 being implanted is a self-expandable prosthetic valve, the prosthetic valve can be retained in a radially compressed configuration within a delivery capsule or sheath (e.g., shaft 218) of the delivery apparatus when inserted into and advanced through the patient's vasculature to the desired implantation site. Once positioned at the desired implantation site, the prosthetic valve can be deployed from the delivery capsule, which allows the prosthetic valve to self-expand to its radially-expanded, functional size within the native valve or a previously implanted host valve. Further details of delivery apparatuses that can be used to deliver and implant self-expandable prosthetic valves (including any of the prosthetic valves disclosed herein when the frames are constructed of a self-expandable material such as Nitinol) are disclosed in U.S. Patent Application Publication Nos. 2014/0343670 and 2010/0049313, which are incorporated herein by reference. When the frame is formed from a self-expandable material, the frame can be shaped set to form the tapered shape when it expands to its fully functional size after being released from the delivery capsule.

In other embodiments, the frame can be constructed by forming individual components (e.g., the struts and fasteners of the frame) and then mechanically assembling and connecting the individual components together. For example, instead of the integrated strut structure illustrated in FIGS. 1-2, the frame can have individual diagonally-extending struts pivotably coupled to one another at one or more pivot joints along the length of each strut, as described in U.S. Patent Application Publication Nos. 2018/0153689, 2018/0344456, and 2019/0060057, all of which are incorporated herein by reference. In some implementations, the individual struts can be helically bent so as to assume the desired tapered profile in the expanded configuration. Further details regarding exemplary constructions of frame 102 and/or prosthetic heart valve 100 are described in U.S. Patent Application Publication Nos. 2020/0188099, 2019/0365530, and 2012/0123529, U.S. Provisional Application Nos. 63/024,951 and 62/869,948, and International Publication No. WO-2020/081893, all of which are incorporated herein by reference.

In the examples illustrated in FIGS. 1-6D, commissure windows 114 are formed as part of the lattice structure of the frame 102. However, in other embodiments, commissure windows 114 may instead be formed in another structure of the frame 102 or as a separate structure attached to the frame 102. For example, in some implementations, the prosthetic heart valve includes one or more actuators coupled to the frame to cause transition of the valve between crimped and expanded configurations, and/or one or more locking mechanisms that maintains a shape of the frame after expansion or contraction. In addition to or in place of commissure windows provided in the lattice structure of the frame, at least one of the actuators or locking mechanisms can include a commissure window formed therein and can be used to mount a commissure tab assembly of the valvular structure thereto. Further details of the actuators, locking mechanisms and delivery apparatuses for actuating the actuators can be found in U.S. Patent Application Publication Nos. 2018/0153689, 2018/0325665, and 2019/0060057, each of which is incorporated herein by reference in its entirety. Any of the actuators and locking mechanisms disclosed in the previously filed applications can be incorporated in any of the prosthetic heart valves disclosed herein. Further, any of the delivery apparatuses disclosed in the previously filed applications can be used to deliver and implant any of the prosthetic heart valves discloses herein.

Alternatively, or additionally, the prosthetic heart valve can include one or more support members (also referred to herein as commissure support portions) that form a part of, or are coupled to, the tapered frame and that include a commissure window. For example, the support member can be an axially extending member that is attached to a radially-inner surface of the frame, and the commissure window can be formed in the support member (e.g., an axially-extending commissure post coupled to the frame, an actuator, or a locking mechanism). Alternatively, or additionally, the commissure window can be formed by a wireform (e.g., bent piece of wire) or clamp coupled to the frame, actuator, locking mechanism, or support member. Further details regarding commissure windows formed from wireforms and commissure windows formed in or on actuators, locking mechanisms, and support members can be found in U.S. Provisional Application No. 62/959,723 and 62/869,948, and International Publication No. WO-2020/102487, both of which are incorporated herein by reference in their entireties.

Figure 9:
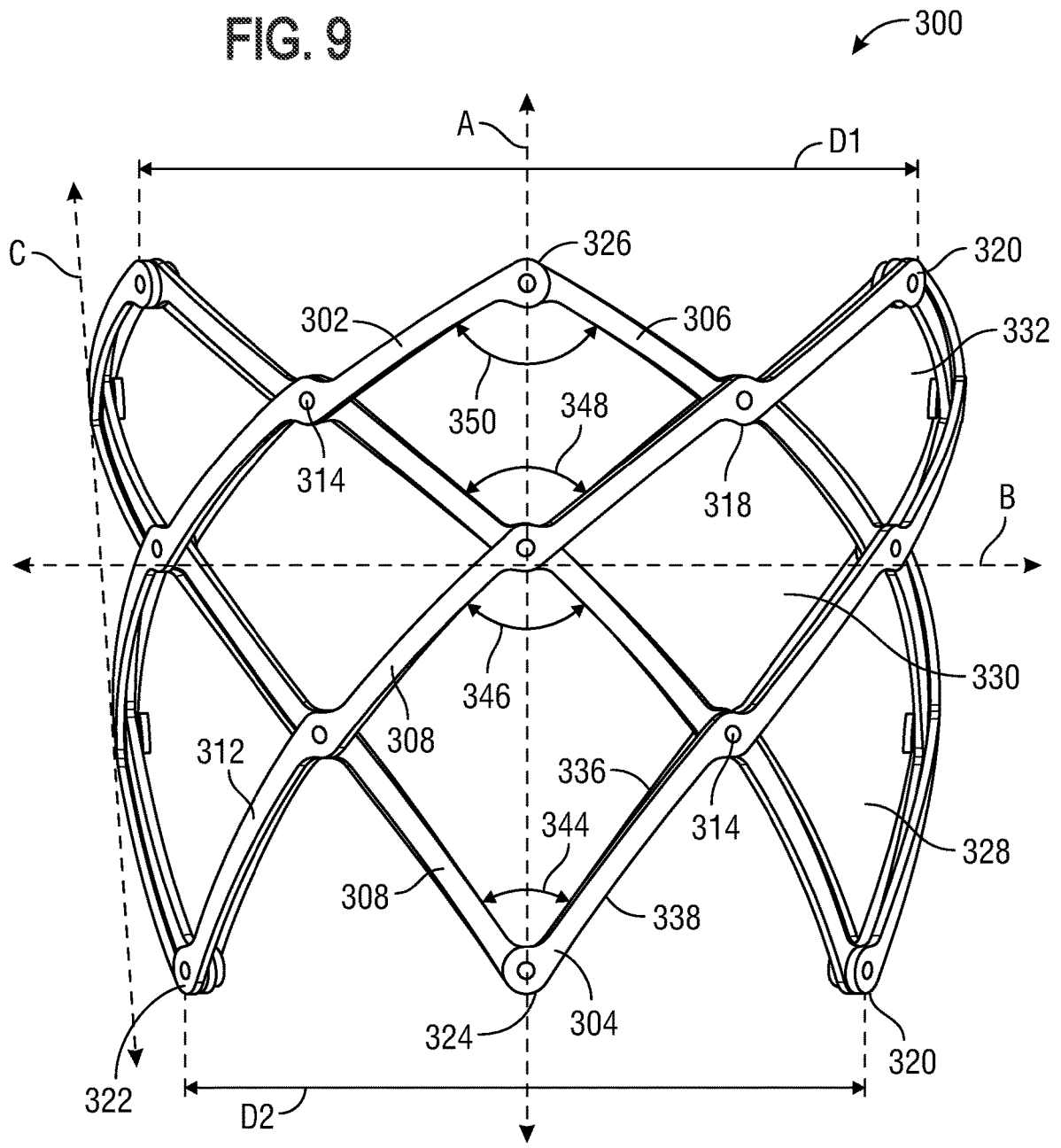
FIG. 9 is a side view of another exemplary tapered frame for a prosthetic heart valve.

For example, FIG. 9 illustrates another example of a prosthetic heart valve 300 comprising a tapered frame 302 shown in its deployed, radially-expanded configuration. The frame 302 can have an inflow end portion 304 defining an inflow end 324 of the frame 302 and an outflow end portion 306 defining an outflow end 326 of the frame 302. The prosthetic valve 300 can define a longitudinal axis (e.g., central longitudinal axis) A extending from the inflow end portion 304 to the outflow end portion 306 and a lateral axis B extending perpendicular to the longitudinal axis A. While only one side of the frame 302 is depicted in FIG. 9, it should be appreciated that frame 302 forms a substantially-frusto-conical structure having an opposite side that is identical to the portion shown.

The frame 302 comprises a plurality of interconnected struts 308 arranged in a lattice-type pattern. Each strut can fully extend from the inflow end 324 of the frame 302 to the outflow end 326 of the frame. Thus, in the illustrated example, the frame 302 can be formed entirely from struts that extend continuously from the inflow end 324 to the outflow end 326. Alternatively, in some implementations, the frame 302 can have struts that are connected end-to-end along the length of the frame. Each of the struts 308 can include a plurality of apertures, which may be spaced unequally along the length of each strut 308 and can define a plurality of segments 312 having unequal lengths. The apertures can be used to connect the struts 308 to one another using fasteners 314. The segments 312 can be arranged end-to-end relative to each other with adjacent ends interconnected to each other by intermediate segments 318. The struts 308 can have enlarged (relative to segments 312) end portions 320 that form apices 322 at the inflow and outflow ends 324, 326 of the frame 302. Each of the intermediate segments 318 and end portions 320 can have a respective aperture, such as at its geometric center, for receiving a fastener 314. In other embodiments, the apertures 310 and/or fasteners 314 can be omitted. For example, the struts 308 can be fixedly connected to one another, such as by welding or adhesion, or by laser-cutting the individual struts of the frame from a metal tube. Each segment 312 can be slightly laterally offset from an adjacent segment 312 in a direction perpendicular to the overall length of the strut 308, as shown in FIG. 9. Alternatively, in some implementations, the segments 312 can be arranged without any offset relative to each other.

In the illustrated example, segments 312 of each strut 308 decrease in length from the inflow end portion 304 to the outflow end portion 306 of the frame 302. In the assembled frame 302, the struts 308 thus define a plurality of open cells arranged in a plurality of circumferentially-extending rows of cells. As shown in FIG. 9, the varying lengths of the strut segments also form angles 344, 346, 348, 350 between pivotably connected struts. A magnitude of the angles 344-350 can progressively increase from the inflow end 324 to the outflow end 326. Alternatively, in some implementations, one or more segments can have unequal lengths and one or more segments can have equal lengths.

In the illustrated example, each strut 308 has five apertures defining four segments 312 and three rows of cells, including a first row of cells 328, a second row of cells 330, and a third row of cells 332. The cells 328 closest to the inflow end 324 can have the largest open area, while the cells 332 closest to the outflow end 326 can have the smallest open area. Alternatively, in some implementations, the cells 332 closest to the outflow end 326 can have the largest open area. Numbers of strut segments (defined by greater of fewer number of apertures) and/or rows of frame cells different than the numbers illustrated in FIG. 9 are also possible according to one or more contemplated embodiments.

As further shown in FIG. 9, each strut 308 can be curved helically with respect to the longitudinal axis A of the frame 302, thereby defining the inverted frustoconical shape of the frame 302. The helical curve provides each strut 308 with a concave, radial inner surface (the surface facing the longitudinal axis A) and an opposing convex, radial outer surface (the surface facing away from the longitudinal axis A). Moreover, each segment 312 of the strut 308 can be curved such that the overall shape of the strut 308 is curved with respect to the lateral axis B (or any line parallel to axis B and perpendicular to axis A).

For example, in some implementations, each strut 308 can have a continuous and constant curve from one end of the strut to the other end of the strut. In other embodiments, the projection of each segment 312 in a plane parallel to the longitudinal axis A can be straight (i.e., each segment 312 is straight except for any helical curvature with respect to the longitudinal axis A) and the amount of offset of each segment 312 relative to an adjacent segment 312 along the length of strut 308 can vary such that the overall shape of the strut 308 is curved along its length with respect to the lateral axis B (or any line parallel to axis B and perpendicular to axis A). In other words, a line extending from one end of the strut to the other end and intersecting each segment 312 can be curved with respect to axis B. Alternatively, individual strut segments 312 can be straight and connected end-to-end to each other at non-zero angles such that the overall shape of the strut 308 is curved along its length with respect to the lateral axis B (or any line parallel to axis B and perpendicular to axis A). In other embodiments, one or more of the struts of a frame can have a non-constant or variable curvature along its length (in which case the center of curvature of the strut can vary as one moves along the length of the strut).

As shown in FIG. 9, each strut 308 can be curved and arranged such that it is convex with respect to the outflow end 326 of the frame 302. As such, each strut 308 in the illustrated example has a convex, first longitudinal edge 336 facing the outflow end 326 of the frame and a concave, second longitudinal edge 338 facing the inflow end 324 of the frame. Due to the unique shape of the struts 308, the frame 302 formed by the struts can have a non-Euclidian geometry, and in particular, an elliptic geometry (also referred to as Riemannian geometry).

As shown in FIG. 9, in the expanded configuration, the curvature of the struts 308 can give the frame 302 a non-cylindrical, tapered shape (e.g., an inverted frustoconical shape, a V-shape, or a Y-shape), with the outflow end 326 having a first diameter $D_1$ larger than a second diameter $D_2$ of the inflow end 324. When implanted within the native annulus of a patient, the larger outflow cross-sectional area relative to the inflow cross-sectional area created by the tapered shape can reduce the pressure gradient across the prosthetic heart valve, which may improve hemodynamics and/or mitigate the risk of paravalvular leakage.

The degree of taper can be defined by the draft angle of the frame 302, which angle is measured between the longitudinal axis A and a line C drawn tangent to the outer surface of the frame. Alternatively, the degree of taper can be defined by the taper angle of the frame 302, which angle is measured between a line C drawn tangent to the outer surface on one side of the frame and another line C drawn tangent to the outer surface on an opposite side of the frame. In some implementations, the taper angle can be less than 10°, for example, 6-8° (corresponding to a draft angle of 3-4°). In some implementations, while in the crimped or radially compressed configuration, the frame 302 can retain a tapered shape, with the outflow end 326 having a diameter larger than a diameter of the inflow end 324. In such embodiments, the draft angle of the frame in the compressed configuration may be greater than the draft angle of the frame in the expanded configuration.

In some implementations, the frame can also have a low-profile (e.g., having a height, H, along the longitudinal axis A between the inflow end 324 and the outflow end 326 that is less than a diameter, $D_2$, of the frame 302 at the inflow end 324). For example, a ratio ($H/D_2$) of the height, H, of the frame to the diameter, $D_2$, at the inflow end can be about 0.63-0.9. Alternatively, or additionally, in some implementations, a ratio ($D_1/H$) of the diameter, $D_1$, of the frame 302 at the outflow end 326 to the height, H, of the frame can be less than about 1.75, for example, in a range of 1.2-1.73, inclusive. As noted above, using such low-profile frames with taper angles of about 6-8° can optimally position the commissures and/or upper free ends of the leaflets to take advantage of the protective features of the annular back flow region during systole.

The prosthetic valve 300 can include a valvular structure (e.g., valvular structure 106 of FIG. 1), inner and/or outer skirts (e.g., inner skirt 108 and outer skirt 104 of FIG. 1), and actuators or locking mechanisms (e.g., as described in the incorporated by reference documents above). Although not separately illustrated, the valvular structure can be constructed and operate similar to valvular structure 106 described above with respect to FIGS. 1-6D. In some implementations, the commissure tab assemblies of the valvular structure are coupled to respective commissure windows of actuators or locking mechanisms that form a part of or are coupled to an interior surface of the frame 302. For example, the commissure tab assemblies can be coupled to the commissure windows of the actuators or locking mechanism in a manner similar to that described above with respect to FIGS. 1-6D. Alternatively, in some implementations, the commissure tab assemblies of the valvular structure are coupled to respective open cells formed by struts of the lattice structure of the frame 302. For example, the commissure tab assemblies can be coupled to the open cells in a manner similar to that described above with respect to FIG. 7. Similar to the examples described above with respect to FIGS. 1-6D, the mounting of the commissure tab assemblies can be such that the leaflets thereof bend at locations at or adjacent to the frame (or at least at or adjacent to the respective commissure window), so as to maximize a cross-sectional area of the outlet of the flow channel formed by the valvular structure in the open configuration. Moreover, similar to the examples described above with respect to FIGS. 1-6D, the commissure tab assemblies and the upper free edge portions of the leaflets can be positioned with respect to frame 302 to take advantage of the protective features of the annular back flow region during systole.

Figure 10A:
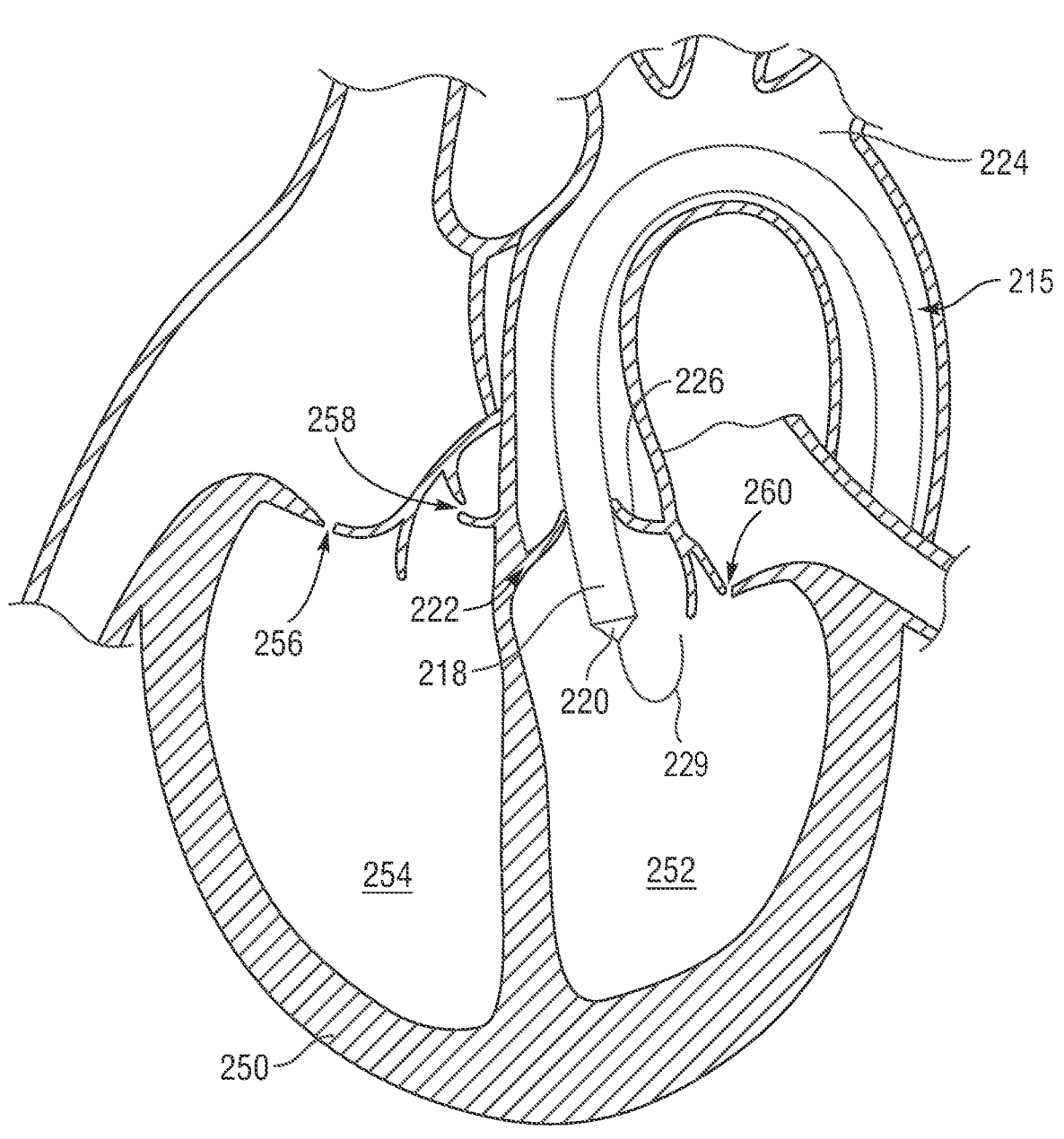
FIGS. 10A-10E depict stages of an exemplary implantation procedure where a prosthetic heart valve is installed within the native aortic valve of a patient's heart.

As noted above, the prosthetic valve 300 can be expanded from an initial compressed configuration to a radially-expanded configuration for mounting within a native heart valve of the patient (or a host valve previously implanted within the patient). For example, for introduction into a patient, the prosthetic valve 300 can be releasably coupled to a delivery apparatus 215 and can be radially compressed by actuating actuators of the valve 300, by tensioning a circumferentially-extending recompression member via a recompression shaft, and/or by inserting the prosthetic valve 300 and delivery apparatus 215 into a crimping device. For example, a first shaft 218 of the delivery apparatus 215 can be advanced over a second shaft 228 of the delivery apparatus and the prosthetic valve 300. The compressed prosthetic valve 300 can thus be disposed within a lumen of the first shaft 218 and a distal end of the first shaft 218 can abut a nosecone 220. A distal end portion of delivery apparatus 215 can then be inserted into a patient's vasculature can be advanced to an implantation location, as shown in FIG. 10A. Note that the illustrated procedure is with respect to a transfemoral delivery of the prosthetic valve; however, other delivery procedures are also possible according to one or more contemplated embodiments, such as transventricular, transapical, transseptal, etc.

Figure 10B:
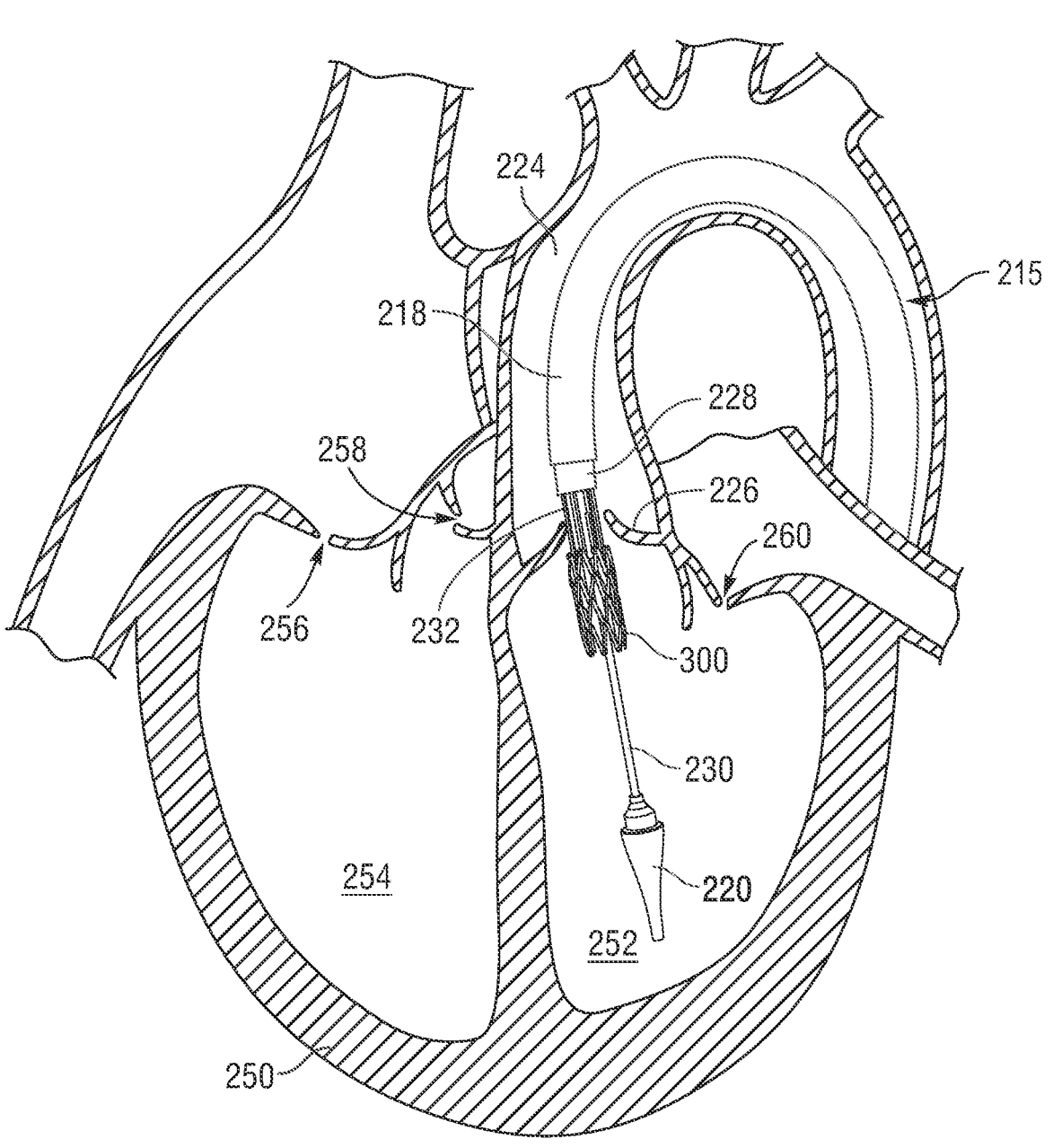

In FIG. 10A, the distal end portion of the delivery apparatus 215 is inserted into the patient's vasculature such that the first shaft 218 extends through the ascending aorta 224 and such that the nosecone 220 extends through the existing valvular structure (e.g., the annulus of the native aortic valve 222 in FIG. 10A) and into the left ventricle 252 of the patient's heart 250. A guidewire 229 can be initially extended through the ascending aorta 224 and used to guide and position the distal end portion of the delivery apparatus 215 within a central region of the aortic valve 222 between leaflets 226 thereof. The delivery apparatus 215 can include an innermost shaft that defines a lumen for the guidewire, as is known in the art. As shown in FIG. 10B, the prosthetic valve 300 can then be deployed from the first shaft 218 of the delivery apparatus, for example, by moving the first shaft 218 proximally relative to the second shaft 228 and/or by moving the second shaft 228 distally relative to the first shaft 218. The first shaft 218 can be moved further proximally such that the support sleeves 232 are exposed from a distal end of the first shaft 218.

Figure 10C:
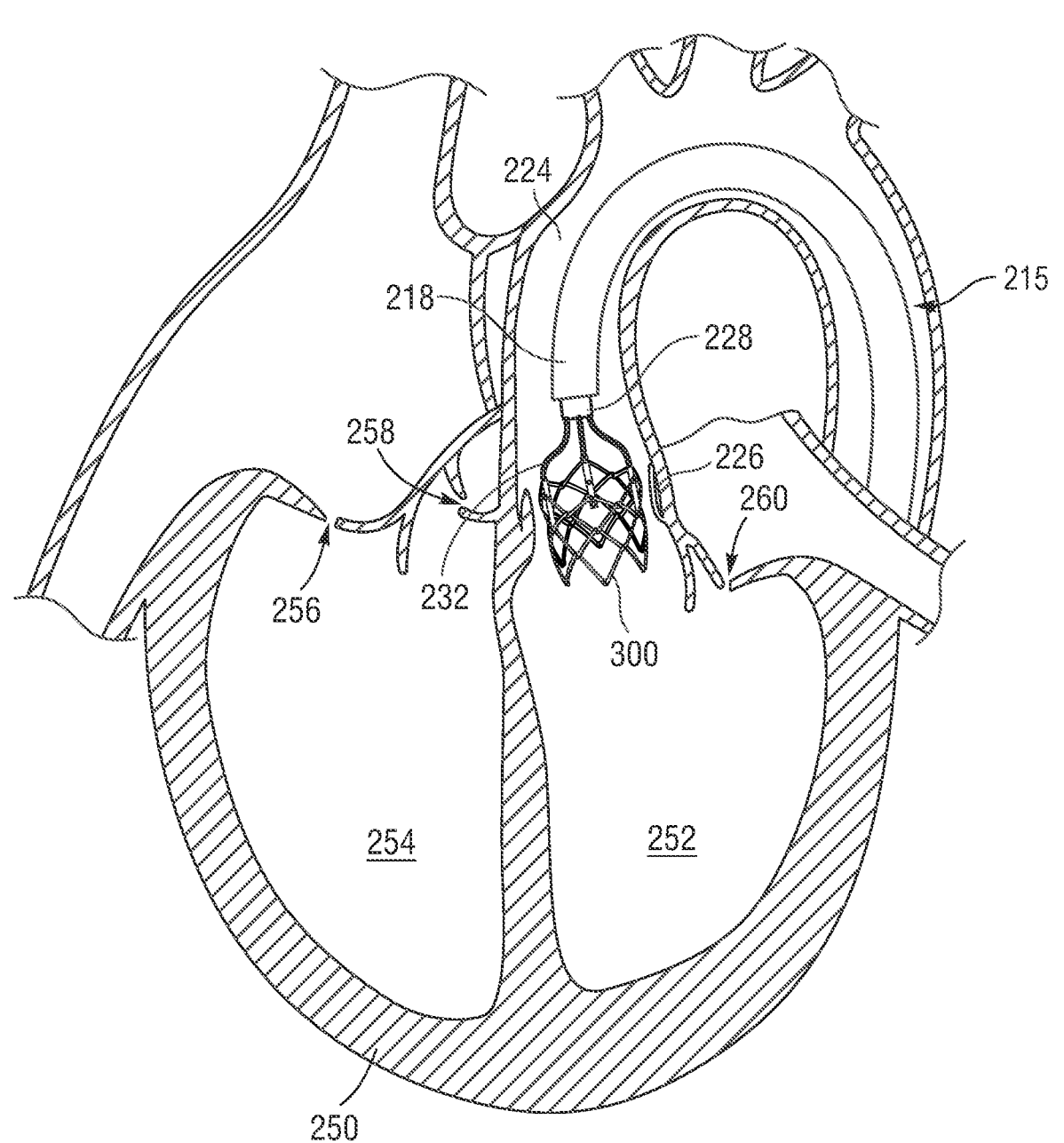
Figure 10D:
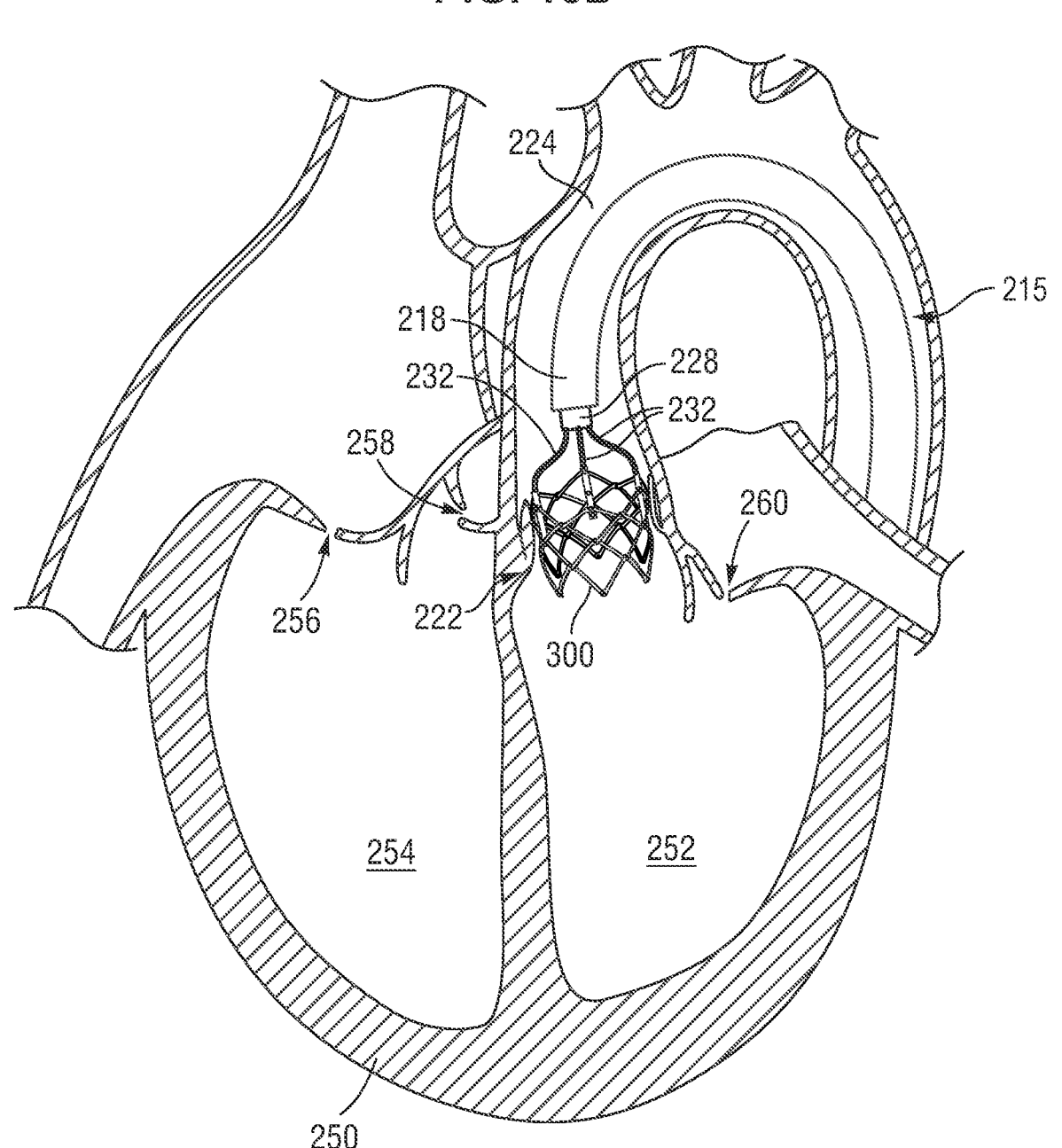
Figure 10E:
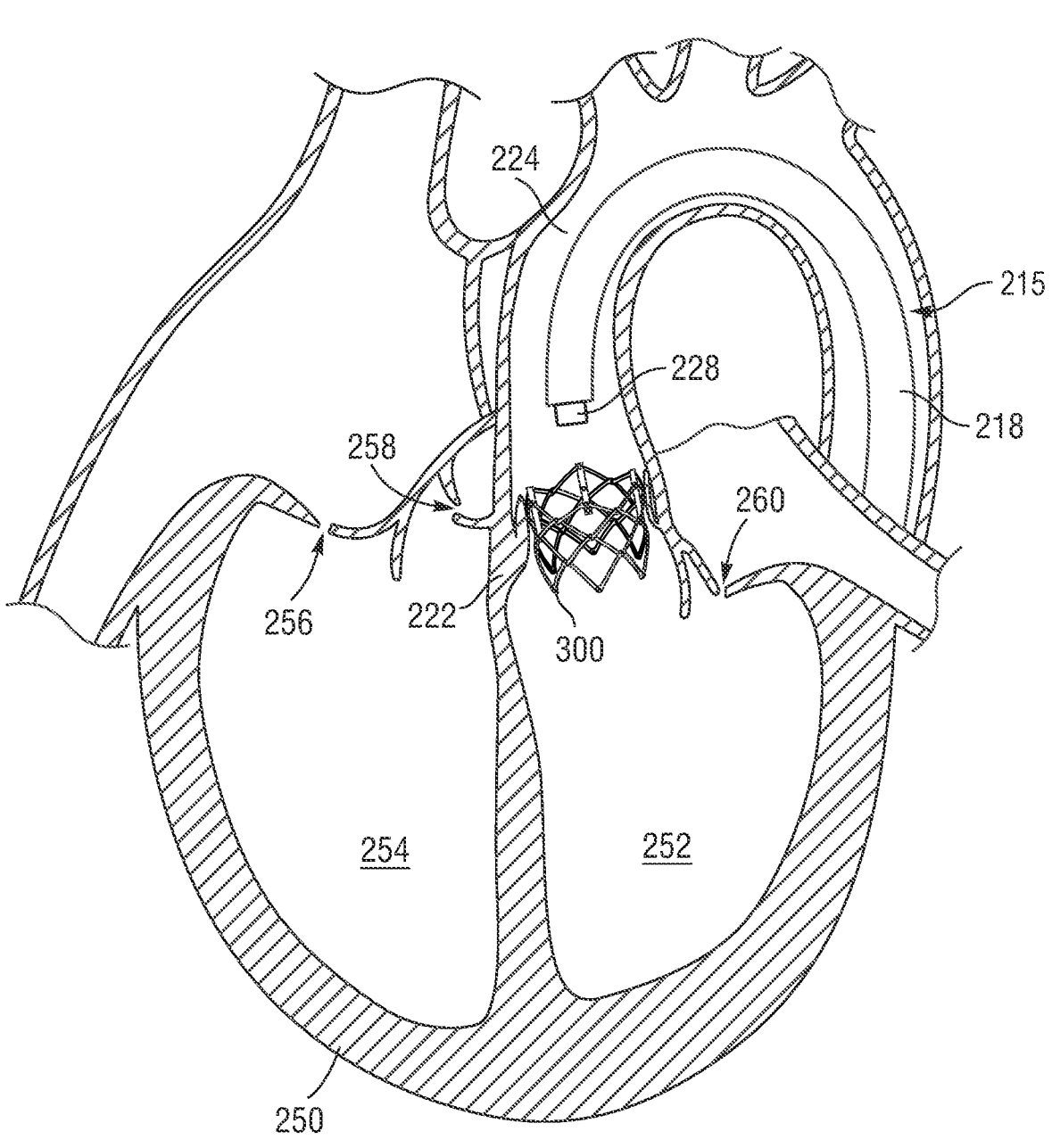

With the prosthetic valve 300 disposed between leaflets 226 of the existing aortic valve 222, the valve 300 can be expanded from the compressed configuration to a deployed configuration, for example, as shown in FIGS. 10C-10D. The expansion can be accomplished by actuation of an actuator of the valve 300, for example, by movement of actuation shafts disposed within support sleeves 232 of the delivery apparatus 215. Alternatively, or additionally, radial expansion of the valve 300 can be accomplished via an inflatable balloon (similar to balloon 214 in FIG. 8) or another type of expansion member (e.g., a self-expanding stent). Once the prosthetic valve 300 has been fully expanded and secured to the surrounding anatomy, it can be released from the delivery apparatus 215, as shown in FIG. 10E. The release can be accomplished by de-coupling the actuation shafts of support sleeves 232 from the valve 300. The support sleeves 232 and the second shaft 228 can then be retracted into the first shaft 218, and delivery apparatus 215 can be removed from the patient's body. Note that for purposes of illustration, the recompression shaft and recompression member are not shown in FIGS. 10A-10E, and the nosecone 1516 and nosecone shaft 1514 are not shown in FIGS. 10C-10E.

Figure 11A:
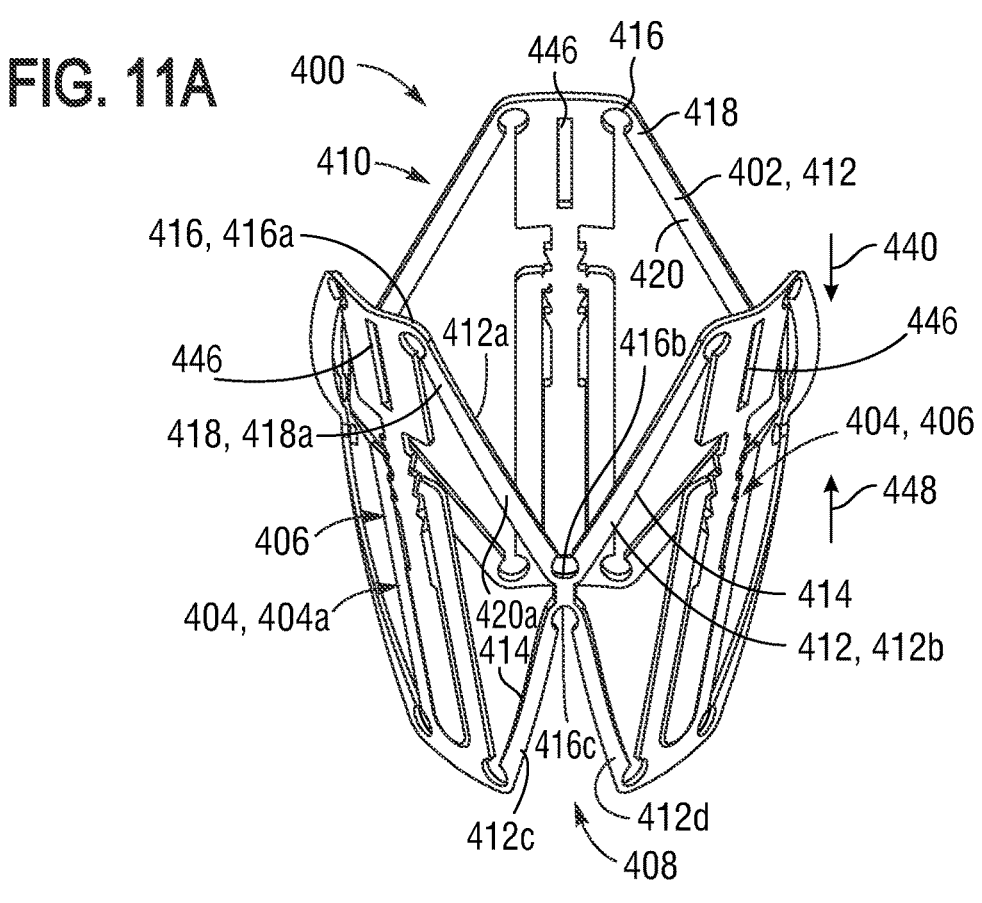
FIGS. 11A-11B are perspective views of another exemplary tapered frame in a partially radially expanded configuration and a radially compressed configuration, respectively.
Figure 11B:
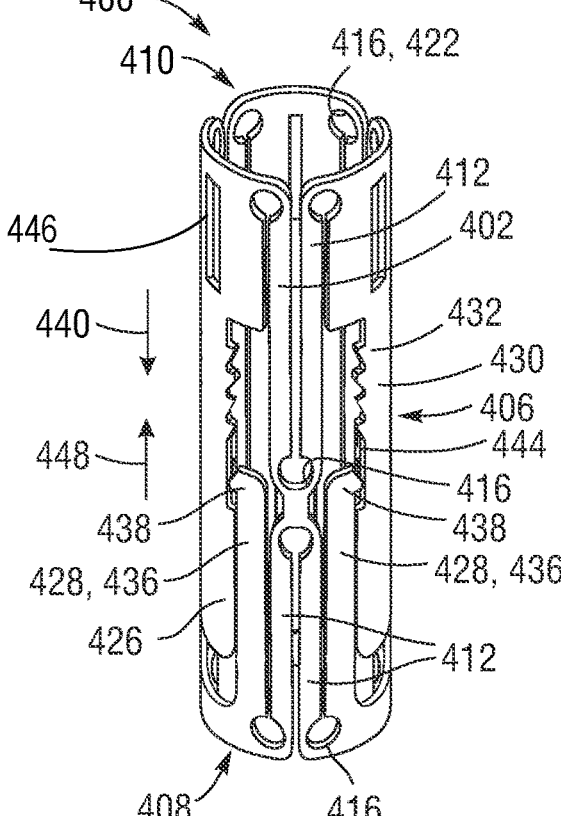

In some implementations, the commissure window can be formed in an outflow end portion of an actuator or locking mechanism that has been integrated into the tapered frame. For example, FIGS. 11A-11B illustrate another example of a prosthetic heart valve 400 comprising a tapered frame 402 in radially-expanded and crimped configurations, respectively. The tapered frame 402 can be formed as a unitary, fastener-free structure. As with the other examples described above, the prosthetic valve 400 can include a valvular structure comprising a plurality of leaflet (such as valvular structure 106 comprising leaflets 110), an inner skirt (such as inner skirt 108), and/or an outer skirt (such as skirt 104), as previously described, although these components have been omitted from FIGS. 11A-11B for purposes of illustration. In the illustrated example, the frame 402 includes one or more posts 404 configured as integral expansion and locking mechanisms 406 which can be used to radially expand the frame 402 and lock the frame 402 in a radially expanded configuration, as described in more detail below. In other embodiments, the frame 402 can comprise one or more separately-formed expansion and locking mechanisms.

The frame 402 can comprise an inflow end portion 408 and an outflow end portion 410. The frame 402 can be a mechanically expandable frame comprising a plurality of posts 404 coupled together by a plurality of rigid members or links 412 (which can also be referred to as "struts"). For example, the frame 402 comprises three posts 404, and each pair of adjacent posts 404 is coupled together by four links 412 defining two generally triangularly shaped cells 414. In the illustrated example, the links 412 are disposed in an X-shape. However, in some implementations, the frame 402 can comprise a greater or fewer number of posts 404 and/or links 412, and the posts 404 and/or links 412 can be disposed in any of a variety of shapes.

Each link 412 can be coupled to one or more adjacent links 412 and/or to an adjacent post 404 via a compliant hinge or joint 416 formed integrally with the frame 402. Each link 412 can have a first end portion 418 and a second end portion 420. The first end portion 418 can be coupled to a post 404 via a first compliant joint 416 and the second end portion 420 can be coupled to an adjacent link 412 via a second compliant joint 416. For example, an exemplary first link 412*a* can have a first end portion 418*a* coupled to a first post 404*a* via a first compliant joint 416*a*, and a second end portion 420*a* coupled to an adjacent second link 412*b* via a second compliant joint 416*b*. The compliant joint 416*b* can be coupled to an additional compliant joint 416*c* connecting links 412*c* and 412*d*. The compliant joints 416 can be configured to allow movement of the links 412 relative to one another and/or the posts 404 via elastic body deformation of the compliant joints 416.

Each compliant joint 416 can comprise a flexible neck portion 422 at least partially defining, for example, a C-shaped cutout including a gap. As the frame 402 moves from a compressed configuration (FIG. 12B) to the expanded configuration (FIG. 12A), the flexible neck portion 422 can deform or deflect circumferentially and the gap can widen. Such a configuration can allow the frame 402 to move between the radially-compressed and radially-expanded configurations without otherwise requiring the use of fasteners to couple adjacent links 412 together. Moreover, the compliant joints 416 can be in-line or flush with the links 412 (e.g., such the compliant joints do not protrude past the radially inner and/or radially outer surfaces of the links 412), thereby reducing the overall crimp profile of the prosthetic valve 400. Such configurations can advantageously eliminate separately formed fasteners (which can be difficult to manufacture and/or install at such a small size) and allow for a single degree of freedom (the pivotable movement between the links 412), thereby preventing or mitigating radial displacement of the links 412, and thus deformation of the frame 402. In addition, the elimination of separately formed fasteners advantageously reduces friction and wear on the frame 402, thereby increasing long-term reliability and precision of the prosthetic valve 400.

In some implementations, the frame 402 can be formed from a unitary piece of material. For example, the frame 402 can be formed using simpler processing and machining procedures such as laser cutting, waterjet cutting, etc. In some particular examples, the frame 402 can be cut (e.g., laser cut) from a tube of material, which can made of any suitable biocompatible metals, such as stainless steel, a nickel-cobalt-chromium alloy (e.g., MP35N), or a nickel-titanium alloy (e.g., Nitinol). In other embodiments, the tube of material can be made of any suitable biocompatible polymeric materials. Furthermore, the absence of fasteners significantly reduces the number of components and simplifies the complexity of assembly, thereby reducing both material and time costs.

Each post 404 (or only some of the posts 404) of the frame 402 can be configured as an expansion and locking mechanism 406. In the illustrated example of FIGS. 12A-12B, the frame 402 has three posts 404, each of which is configured as an expansion and locking mechanism 406. Alternatively, in some implementations, the frame 402 can have more or less than three posts, all, or less than all, of which can be configured as expansion and locking mechanisms. Each expansion and locking mechanism 406 can comprise a rachet mechanism or rachet assembly comprising an inner member 426 and one or more outer members 428. The inner and/or outer members 426, 428 can extend from and be formed integrally with a respective end of the frame 402. For example, in the illustrated example, the inner member 426 extends from the outflow end 410 of the frame 402 toward the inflow end 408 and the one or more outer members 428 extend from the inflow end 408 of the frame toward the outflow end 410. Alternatively, in some implementations, the inner member 426 can extend from the inflow end 408 of the frame 402, and the one or more outer members 428 can extend from the outflow end 410 of the frame. Alternatively, in still other embodiments, the inner and/or outer members 426, 428 can be formed separately from the frame 402 and coupled thereto using, for example, welding, adhesives, and/or mechanical fasteners such as screws or pins.

The inner member 426 can comprise one or more linear racks 430 each including a plurality of teeth 432. The one or more linear racks 430 can be disposed on one or more circumferential edges of the inner member 426. In the illustrated example, the inner member 426 comprises two linear racks 430, one disposed on each circumferential edge of the inner member 426. However, in some implementations, the inner member 426 can comprise only a single linear rack 430. One or more of the outer members 428 can comprise a pawl 436 configured to engage the teeth 432 of the linear rack(s) 430. Each pawl 436 can comprise an elongated body terminating in a locking tooth 438 that can engage the teeth 432 of the linear rack 430.

The pawl 436 and the teeth 432 can be configured such that when the pawl 436 is engaged with the rack 430, the inner member 426 and the one or more outer members 428 can move relative to one another in a first axial direction, but are prevented from moving relative to one another in a second, opposite axial direction. For example, when the pawl 436 is engaged with the linear rack 430, the inner member 426 can move axially toward the inflow end (e.g., direction 440) but cannot move axially toward the outflow end (e.g., direction 448). This ensures that when the pawl 436 is engaged with the rack 430, the frame 402 can be radially expanded but cannot be radially compressed. In other words, the inflow end 408 and the outflow end 410 of the frame 402 can move axially toward one another but cannot move axially away from one another. Once the prosthetic valve 400 has been implanted within a selected implantation site within a patient, the patient's native anatomy (e.g., the native aortic annulus) may exert radial forces against the prosthetic valve 400 that would tend to compress the frame 402. However, the engagement between the pawl 436 and the rack 430 prevents such forces from compressing the frame 402, thereby ensuring that the frame remains locked in the desired radially expanded configuration.

In some implementations, such as the illustrated example, the inner member 426 can comprise a toothless portion 444 adjacent the linear rack 430. The toothless portion 444 can be disposed nearer the inflow end than the linear rack 430, and can be a recessed, flat portion of the inner member. The toothless portion 444 can configured to allow bi-directional axial movement (in the distal and proximal directions) of the inner member 426 relative to the outer members 428, for example, to allow the frame 402 to expand and/or compress prior to engagement of the pawl(s) 436 with the plurality of teeth 432.

As shown in FIG. 11A, in the expanded configuration, the frame 402 can be shaped to adopt a non-cylindrical, tapered shape (e.g., an inverted frustoconical shape, a V-shape, or a Y-shape) in the radially-expanded configuration, such that the outflow end 410 has a diameter larger than the diameter at the inflow end 408. Similar to the above-described examples, the degree of taper of frame 402 can be defined by the draft angle (e.g., as measured between a central longitudinal axis of the frame 402 and one of the outer sidewalls formed by the struts 412 of the frame 402) or the taper angle (e.g., as measured between outer sidewalls on opposite sides of a diameter of the frame 402). In some implementations, the taper angle can be less than 10°, for example, 6-8° (corresponding to a draft angle of 3-4°). In some implementations, while in the crimped or radially compressed configuration, the frame 402 can retain a tapered shape, with the outflow end 410 having a diameter larger than a diameter of the inflow end 408. In such embodiments, the draft angle of the frame in the compressed configuration may be greater than the draft angle of the frame in the expanded configuration.

In some implementations, the frame can also have a low-profile (e.g., having a height along the longitudinal axis between the inflow end 408 and the outflow end 410 that is less than a diameter of the frame 402 at the inflow end 408). For example, a ratio ($H/D_2$) of the height, H, of the frame to the diameter, $D_2$, at the inflow end 408 can be about 0.63-0.9. Alternatively or additionally, in some implementations, a ratio ($D_1/H$) of the diameter, $D_1$, of the frame 402 at the outflow end 410 to the height, H, of the frame can be less than about 1.75, for example, in a range of 1.2-1.73, inclusive. As noted above, using such low-profile frames with taper angles of about 6-8° can optimally position the commissures and/or upper free ends of the leaflets to take advantage of the protective features of the annular back flow region during systole.

Figure 11C:
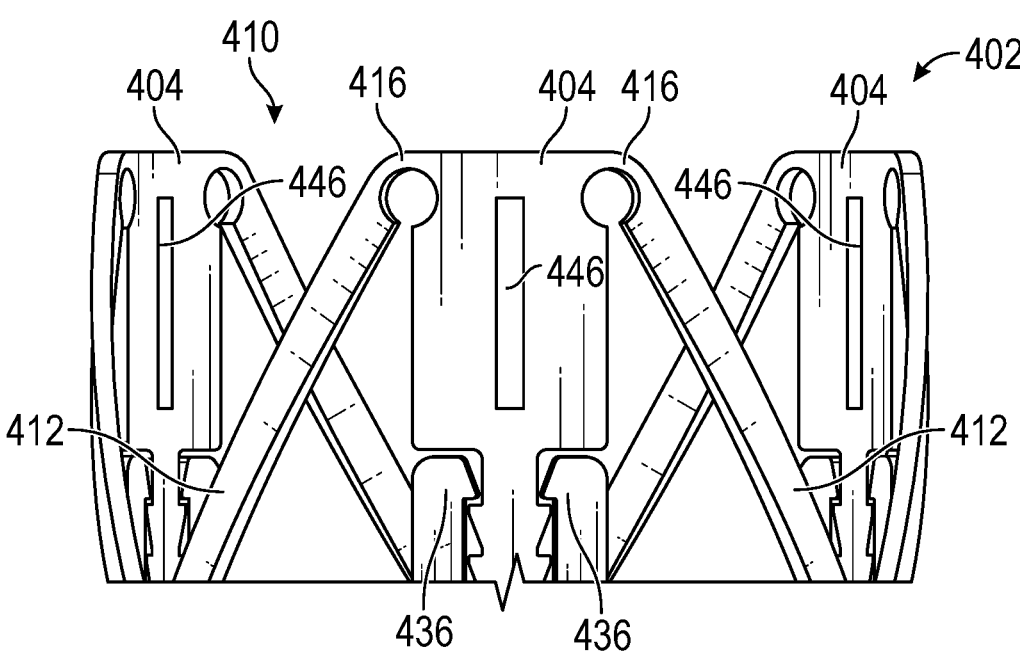
FIG. 11C is a side elevation view of a portion of the frame of FIG. 11A.

The prosthetic valve 400 can include a valvular structure (e.g., valvular structure 106 of FIG. 1) and inner and/or outer skirts (e.g., inner skirt 108 and outer skirt 104 of FIG. 1). Although not separately illustrated in FIGS. 11A-11C, the valvular structure can be constructed and operate similar to valvular structure 106 described above with respect to FIGS. 1-6D. For example, the inflow or cusp edges of the leaflets 110 can be connected to an inner and/or outer skirt via sutures, in a manner similar to that shown in FIG. 1. Alternatively, or additionally, the inflow or cusp edges of the leaflets can be connected to adjacent links 412.

In some implementations, each post 404 can further comprise a commissure opening or slot 446, to which commissure tab assemblies of the leaflets 110 can be mounted. The commissure opening 446 can extend radially through a thickness of the post 404 and can be configured to accept commissure tab assemblies therein to couple the valvular structure to the frame 402. In the illustrated example, the commissure opening 446 has a rectangular shape and is fully enclosed by the post 404 (e.g., the opening 446 does not extend to an inflow and/or outflow edge of the post 404). However, in other embodiments, the commissure opening 446 can have any of various shapes (e.g., square, oval, square-oval, triangular, L-shaped, T-shaped, C-shaped, etc.). In some implementations, the opening 446 can extend to an edge of the post 404 (e.g., an outflow edge) such that a portion of the valvular structure can be inserted axially (rather than, or in addition to, radially) into the commissure opening 446.

Figure 11D:
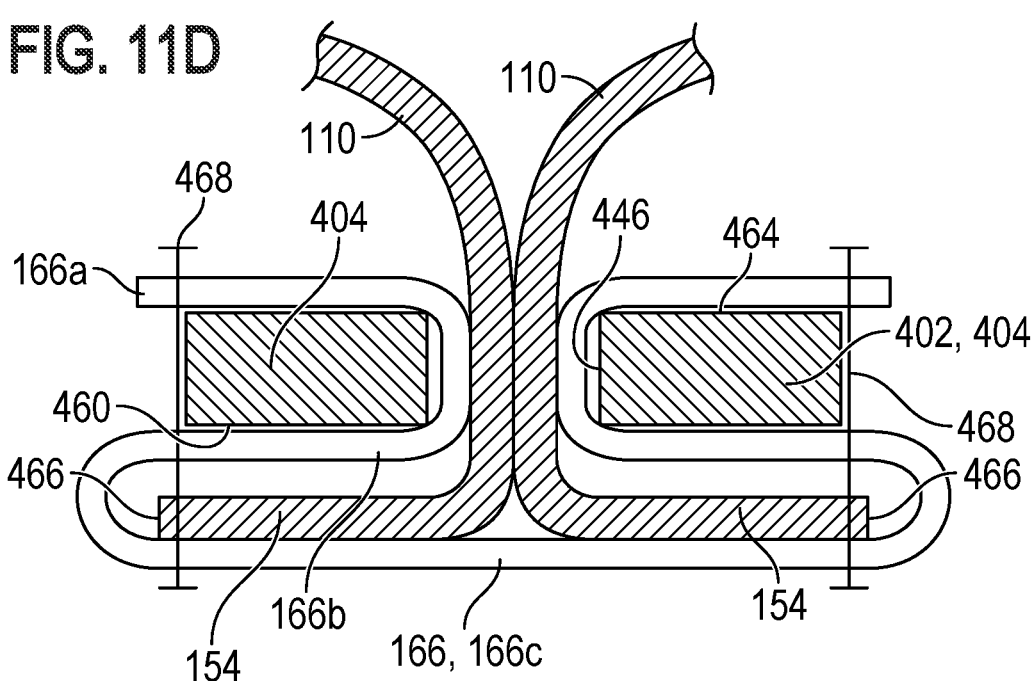
FIG. 11D is a cross-sectional view illustrating an exemplary coupling of a valvular structure to a commissure portion of the frame of FIG. 11A.

In some implementations, a valvular structure including a plurality of leaflets 110 can be coupled to the frame 402 in the following exemplary configuration. FIG. 11D illustrates a cross-sectional view of a portion of a post 404 of the frame 402. Tab portions 154 of adjacent leaflets 110 can extend through the commissure opening 446 and can be folded along the radially outer surface 460 of the frame 402. A coupling member 166 (e.g., a flexible connector comprising a fabric) can extend along a radially inner surface 464 of the frame 402, through the opening 446, around the outer edges 466 of each tab 458, and across the radially outer surface of the tabs 458, such that the coupling member forms a plurality of layers (e.g., first, second, and third layers 166a-166c in the illustrated example). The various components can be coupled together using one or more sutures 468. In the illustrated example, each suture 468 extends through the first and second layers 166a, 166b of the coupling member, through the leaflet tab 154, and through the third layer 166c. Alternatively, in some implementations, the commissure tab assemblies can be coupled to the commissure openings in a manner similar to that described above with respect to FIGS. 1-6D. Alternatively, in some implementations, the commissure tab assemblies of the valvular structure are coupled to respective open cells formed by struts 412 of frame 402, for example, in a manner similar to that described above with respect to FIG. 7. Further details regarding commissure tab assemblies and additional commissure configurations useable with frame 402 can be found, at least, in U.S. Pat. No. 9,393,110, U.S. Patent Application Publication Nos. 2018/0325665 and 2019/01051153, and U.S. Provisional Application No. 63/049,812, which are all incorporated by reference herein in their entireties.

In some implementations, similar to the examples described above with respect to FIGS. 1-6D, the mounting of the commissure tab assemblies to frame 402 can be such that the leaflets 110 thereof bend at locations at or adjacent to the frame 402 (or at least at or adjacent to the respective commissure opening 446), so as to maximize a cross-sectional area of the outlet of the flow channel formed by the valvular structure in the open configuration. Moreover, similar to the examples described above with respect to FIGS. 1-6D, the commissure tab assemblies and the upper free edge portions of the leaflets can be positioned with respect to frame 402 to take advantage of the protective features of the annular back flow region during systole.

The prosthetic valve 400 can be implanted within a patient in the following exemplary manner. For example, the prosthetic valve 400 can be placed in the radially-compressed configuration (FIG. 11D) and releasably coupled to a distal end portion of a delivery apparatus, such as delivery apparatus 210 in FIG. 8 or delivery apparatus 215 in FIGS. 10A-10E. The distal end portion of the delivery apparatus with the prosthetic valve 400 can then be advanced through the vasculature of a patient to a selected implantation site. For example, when replacing the native aortic valve, the prosthetic valve 400 and the distal end of the delivery apparatus can be advanced through the aorta to position the prosthetic valve 400 within the native aortic valve annulus. If retained within a delivery sheath, the delivery sheath can be retracted, or the prosthetic valve can be advanced distally from the sheath. The prosthetic valve 400 can then be expanded to its desired functional size and locked into place using the expansion and locking mechanisms 406. The prosthetic valve 400 can also be delivered and implanted within the other native valves of the heart (the mitral valve, the tricuspid valve, and the pulmonary valve) using any known delivery approaches.

In some implementations, each expansion and locking mechanism 406 can be releasably coupled to a respective actuation assembly of a delivery apparatus, for example, members similar to support sleeves 232 of delivery apparatus 215. In some implementations, the actuation assembly can comprise a first actuation member (e.g., a support tube) and a second actuation member (e.g., a tension member or pull cable), with the second actuation member extending through the first actuation member. One or both of the first and second actuation members can engage with or be coupled to respective portions of the prosthetic heart valve 400, thereby allowing the delivery apparatus to apply a force to valve 400 that causes it to expand from the initial crimped configuration to the final deployed configuration (or any intermediate configurations defined by the expansion and locking mechanism 406).

For example, the delivery apparatus can be used to apply a distally-directed force (as shown by arrow 440) to an outflow end portion of the expansion and locking mechanism 406 via the first actuation member of the delivery apparatus, and a proximally-directed force (as shown by arrow 448) to an inflow end portion of the expansion and locking mechanism 406 via the second actuation member of the delivery apparatus. The opposingly-directed forces by the delivery apparatus actuation assembly can move the inner member 426 and the outer members 428 axially relative to one another in a telescoping manner to cause the frame to radially expand. Once the prosthetic valve 400 has been implanted at a selected implantation within a patient, the patient's native anatomy (e.g., the native aortic annulus)

may exert radial forces on the prosthetic heart valve 400 that would tend to compress the frame 402. However, the radial forces applied by the native anatomy are orthogonal to the degree of freedom of the plurality of compliant joints 416, which advantageously allows the compliant joints 416 to spread the forces across the entire frame 402, thereby preventing the radial forces from compressing the frame 402, while the engagement between locking tooth 438 of pawl 436 and teeth 432 of linear rack 430 ensures that the frame remains locked in the desired radially-expanded configuration.

In any of the disclosed examples or embodiments, a coupling member, which may be formed of flexible cloth or fabric, can be disposed around surfaces of the leaflet tabs and or the wedge member(s). For example, the coupling member can be attached to the wedge member(s) and the tabs prior to installation in the commissure window. In some implementations, the coupling member can be wrapped around portions of the commissure window (e.g., struts 132) to further secure the leaflet tabs to the commissure window and/or protect portions of the leaflets from abrasion, similar to the configuration illustrated in FIG. 11D.

Figure 8:
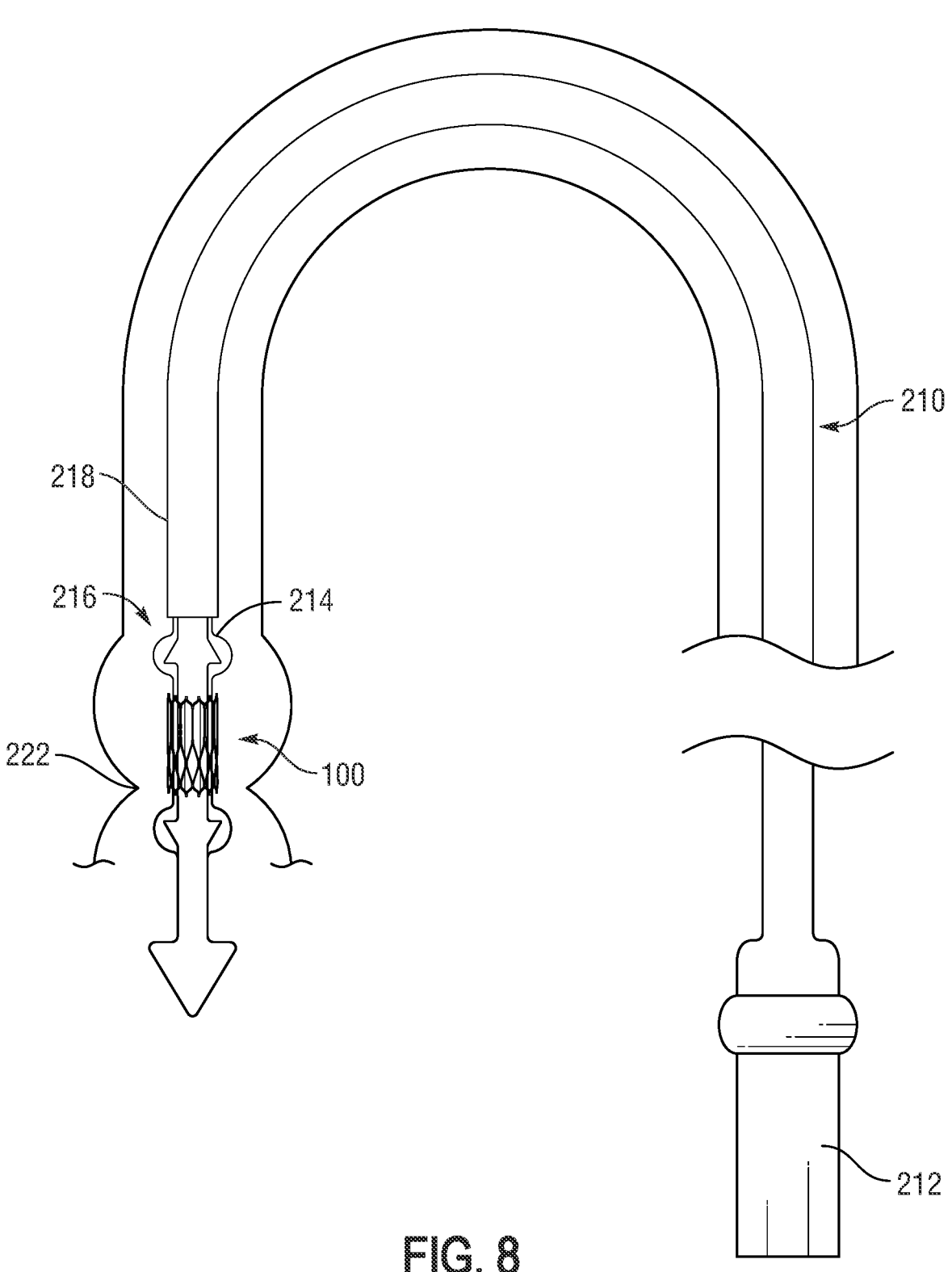
FIG. 8 is a side view of an example of a prosthetic valve being implanted within a native aortic valve of a heart, which is partially shown.

All features described herein are independent of one another and, except where structurally impossible, can be used in combination with any other feature described herein. For example, a delivery apparatus 210 as shown in FIG. 8 can be used in combination with prosthetic valves 300 and/or 400 described herein, and a delivery apparatus as shown in FIGS. 10A-10E can be used in combination with prosthetic valves 100 and/or 400. In another example, the valvular structure 106, as shown in and described with respect to FIGS. 5A-6C, can be used in combination with the prosthetic valve 300 shown in FIG. 9 and/or prosthetic valve 400 shown in FIGS. 11A-11D. In yet another example, the various exemplary mountings of commissure tab assemblies to prosthetic heart valve frames, as illustrated in FIGS. 4A-4B, 6D, 7, and/or 11D can be used with any of the disclosed prosthetic valves or variations thereof.

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1

A prosthetic heart valve comprises a frame that is expandable between a crimped configuration and an expanded configuration and a valvular structure comprising a plurality of leaflets. Each leaflet has a pair of tabs. The tabs of the pair are on opposite sides from each other with respect to a centerline of the leaflet. The valvular structure has a plurality of commissure tab assemblies formed by paired tabs of adjacent leaflets. The valvular structure is coupled to the frame via the plurality of commissure tab assemblies. The frame has an inflow end and an outflow end separated from the inflow end along an axial direction of the frame. The inflow end of the frame has a first diameter in the crimped configuration and a second diameter greater than the first diameter in the expanded configuration. The outflow end of the frame has a third diameter in the crimped configuration and a fourth diameter greater than the third diameter in the expanded configuration. The frame in the expanded configuration has an inverted frustoconical shape, with the fourth diameter of the outflow end being greater than the second diameter of the inflow end. A taper angle of the inverted frustoconical shape of the frame in the expanded configuration is 6-8°, inclusive. The frame in the expanded configuration has a height along the axial direction from the inflow end to the outflow end. A ratio of the height of the frame in the expanded configuration to the second diameter of the inflow end is 0.63-0.9, inclusive. The valvular structure is constructed to transition between a closed configuration, where the leaflets prevent blood flow from the inflow end to the outflow end of the frame, and an open configuration, where the leaflets deflect away from a central axis of the frame to form a flow channel from the inflow end to the outflow end of the frame. The flow channel formed by the valvular structure in the open configuration is tapered such that a cross-sectional area at an outlet of the flow channel is greater than a cross-sectional area at an inlet of the flow channel.

Example 2

The prosthetic heart valve according to any example herein, particularly example 1, wherein the prosthetic heart valve is constructed such that blood flow through the flow channel of the valvular structure in the open configuration produces an annular back flow region adjacent to a radially-inner circumferential surface of the frame, and the commissure tab assemblies are positioned at respective locations along the axial direction within the annular back flow region.

Example 3

The prosthetic heart valve according to any example herein, particularly any of examples 1-2, wherein in transitioning between the open configuration and the closed configuration, each leaflet bends about a respective bending axis, and each bending axis is disposed at or substantially adjacent to a radially-inner circumferential surface of the frame where the valvular structure is coupled via the respective commissure tab assembly.

Example 4

The prosthetic heart valve according to any example herein, particularly any of examples 1-3, wherein a ratio of the fourth diameter of the outflow end to the height of the frame is less than 1.75.

Example 5

The prosthetic heart valve according to any example herein, particularly any of examples 1-4, wherein the ratio of the fourth diameter of the outflow end to the height of the frame is within a range of 1.2-1.73, inclusive.

Example 6

The prosthetic heart valve according to any example herein, particularly any of examples 1-5, wherein the cross-sectional area of the flow channel varies in a substantially linear manner along the axial direction from the inlet of the flow channel to the outlet of the flow channel.

Example 7

The prosthetic heart valve according to any example herein, particularly any of examples 1-6, wherein the flow channel extends substantially parallel to and coaxial with the frame.

Example 8

The prosthetic heart valve according to any example herein, particularly any of examples 1-7, wherein the frame comprises a plurality of commissure windows, and each commissure tab assembly is coupled to a corresponding one of the commissure windows to support the valvular structure within the frame.

Example 9

The prosthetic heart valve of example 8, wherein the commissure tab assemblies are coupled to the commissure windows via respective tab portions on a radially-outer side of the frame.

Example 10

The prosthetic heart valve according to any example herein, particularly any of examples 8-9, wherein, at each commissure tab assembly, portions of the tabs of the leaflets on a radially-outer side of the frame are coupled to one or more struts of the respective commissure window by one or more sutures.

Example 11

The prosthetic heart valve according to any example herein, particularly any of examples 8-10, wherein each commissure tab assembly comprises a coupling member that wraps around the portions of the tabs of the leaflets on a radially-outer side of the frame.

Example 12

The prosthetic heart valve according to any example herein, particularly any of examples 8-11, wherein the coupling member comprises a flexible cloth or fabric.

Example 13

The prosthetic heart valve according to any example herein, particularly any of examples 1-12, wherein the frame comprises a plurality of struts that define a plurality of open cells.

Example 14

The prosthetic heart valve according to any example herein, particularly any of examples 13, wherein the tabs of each commissure tab assembly are coupled to struts that surround and define a respective one of the open cells.

Example 15

The prosthetic heart valve of example 14, wherein the tabs of each commissure tab assembly are coupled to the struts by a coupling member disposed within the respective open cell and extending between surrounding struts defining the respective open cell.

Example 16

The prosthetic heart valve of example 15, wherein each coupling member is coupled to the struts by one or more first sutures, and each tab of the corresponding commissure tab assembly is attached to the coupling member by one or more second sutures.

Example 17

The prosthetic heart valve according to any example herein, particularly any of examples 14-16, wherein the tabs of each commissure tab assembly are separated and folded to form a T-shape, such that each tab comprises a first portion that extends along a circumferential direction of the frame and contacts the coupling member, and a second portion that extends along a radial direction of the frame, contacts the corresponding second portion of the other tab of the pair, and connects the first portion to a central portion of the leaflet.

Example 18

The prosthetic heart valve according to any example herein, particularly any of examples 13-17, wherein the open cells are at an outflow end of the prosthetic heart valve.

Example 19

The prosthetic heart valve according to any example herein, particularly any of examples 15-18, wherein the coupling member comprises a flexible cloth or fabric.

Example 20

The prosthetic heart valve according to any example herein, particularly any of examples 13-19, wherein the frame comprises a plurality of interconnected and angled struts defining a plurality of rows of cells arranged between the outflow end and the inflow end of the frame, and each strut is connected to other struts at intermediate and end portions by respective fasteners, such that the struts can pivot about each fastener to transition between the crimped and expanded configurations.

Example 21

The prosthetic heart valve according to any example herein, particularly any of examples 13-19, wherein the frame comprises a plurality of integrally-formed and angled struts defining a plurality of rows of cells arranged between the outflow end and the inflow end of the frame.

Example 22

The prosthetic heart valve according to any example herein, particularly any of examples 1-13, wherein the frame comprises a plurality of interconnected and angled struts; and a plurality of commissure support portions, each commissure support portion being arranged on one of a support post, actuator, or expansion/locking mechanism of the frame, each commissure tab assembly being coupled to a corresponding one of the commissure support portions.

Example 23

The prosthetic heart valve according to any example herein, particularly any of examples 1-13, wherein the frame comprises a plurality of support members integrally formed with or coupled to struts of the frame, and each support member comprises a commissure window, each commissure tab assembly being coupled to a corresponding one of the commissure windows to support the valvular structure within the frame.

Example 24

The prosthetic heart valve according to any example herein, particularly example 23, wherein the frame comprises an actuator constructed to expand or contract the frame, or a locking mechanism constructed to maintain a shape of the frame after expansion or contraction thereof, and at least one of the support members is a portion of the actuator or locking mechanism, or is coupled to the actuator or locking mechanism.

Example 25

The prosthetic heart valve of example 23, wherein the frame comprises a plurality of integral expansion/locking (IEL) mechanisms, each IEL mechanism extending along a radial direction of the frame between struts, the IEL mechanisms being constructed to lock the frame at the expanded configuration or at one or more intermediate configurations between the crimped and expanded configurations.

Example 26

The prosthetic heart valve according to any example herein, particularly any of examples 23-25, wherein the struts include compliant hinges or joints, such that the struts flex at each hinge or joint to transition between the crimped and expanded configurations.

Example 27

The prosthetic heart valve according to any example herein, particularly any of examples 1-26, further comprising a circumferential outer skirt disposed on a radially-outer side of the frame and coupled thereto, the outer skirt being at or adjacent to the inflow end.

Example 28

The prosthetic heart valve according to any example herein, particularly any of examples 1-27, further comprising a circumferential inner skirt disposed on a radially-inner side of the frame and coupled thereto, the inner skirt being at or adjacent to the inflow end, wherein each leaflet is coupled to the inner skirt at respective cusp edge portions.

Example 29

The prosthetic heart valve according to any example herein, particularly any of examples 1-28, wherein the valvular structure is a bicuspid structure with two leaflets and two commissure tab assemblies, and the valvular structure is coupled to the frame via the commissure tab assemblies on diametrically opposite sides of the frame from each other.

Example 30

The prosthetic heart valve according to any example herein, particularly any of examples 1-28, wherein the valvular structure is a tricuspid structure with three leaflets and three commissure tab assemblies, and the valvular structure is coupled to the frame via the three commissure tab assemblies equally spaced along a circumferential direction of the frame.

Example 31

The prosthetic heart valve according to any example herein, particularly any of examples 1-30, wherein the frame is formed of a plastically-expandable material or a self-expanding material.

Example 32

A prosthetic heart valve comprises a frame that is expandable between a crimped configuration and an expanded configuration; and a valvular structure comprising a plurality of leaflets, each leaflet having a pair of tabs and an upper free edge portion extending between the tabs, the valvular structure having a plurality of commissure tab assemblies formed by paired tabs of adjacent leaflets, the valvular structure being coupled to the frame via the plurality of commissure tab assemblies. The frame has an inflow end and an outflow end separated from the inflow end along an axial direction of the frame. The frame in the expanded configuration has a first inverted frustoconical shape, with a first diameter at the outflow end that is greater than a second diameter at the inflow end. The valvular structure is constructed to transition between a closed configuration, where the leaflets prevent blood flow from the inflow end to the outflow end of the frame, and an open configuration, where the leaflets form a flow channel from the inflow end to the outflow end of the frame. In transitioning between the open configuration and the closed configuration, each leaflet bends about a respective bending axis at each tab, and each bending axis is disposed at or substantially adjacent to a radially-inner circumferential surface of the frame where the valvular structure is coupled via the respective commissure tab assembly. The flow channel formed by the valvular structure in the open configuration adopts a second inverted frustoconical shape, with a cross-sectional area at an outlet of the flow channel that is greater than a cross-sectional area at an inlet of the flow channel. The second inverted frustoconical shape has a sidewall extending between the inlet and the outlet of the flow channel that is substantially parallel to a facing sidewall of the first inverted frustoconical shape between the inflow and outflow ends of the frame. The prosthetic heart valve is constructed such that blood flow through the flow channel of the valvular structure in the open configuration produces an annular back flow region adjacent to a radially-inner circumferential surface of the frame. The commissure tab assemblies are positioned at respective locations along the axial direction within the annular back flow region such that the back flow urges the upper free edge portions of the leaflets from contacting the frame when blood flows through the flow channel of the valvular structure in the open configuration.

Example 33

The prosthetic heart valve according to any example herein, particularly example 32, wherein, in the expanded configuration, the frame has a height along the axial direction from the inflow end to the outflow end that is less than the second diameter at the inflow end.

Example 34

The prosthetic heart valve according to any example herein, particularly example 33, wherein a ratio of the height of the frame in the expanded configuration to the second diameter of the inflow end is within a range of 0.63-0.9, inclusive.

Example 35

The prosthetic heart valve according to any example herein, particularly any of examples 32-34, wherein a taper angle of the first inverted frustoconical shape of the frame in the expanded configuration is within a range of 6-8°, inclusive.

Example 36

The prosthetic heart valve according to any example herein, particularly any of examples 33-35, wherein a ratio of the first diameter of the outflow end to the height of the frame is less than 1.75.

Example 37

The prosthetic heart valve according to any example herein, particularly any of examples 33-36, wherein a ratio of the first diameter of the outflow end to the height of the frame is within a range of 1.2-1.73, inclusive.

Example 38

The prosthetic heart valve according to any example herein, particularly any of examples 32-37, wherein the cross-sectional area of the flow channel varies in a substantially linear manner along the axial direction from the inlet of the flow channel to the outlet of the flow channel.

Example 39

The prosthetic heart valve according to any example herein, particularly any of examples 32-38, wherein the frame comprises a plurality of commissure windows, and each commissure tab assembly is coupled to a corresponding one of the commissure windows to support the valvular structure within the frame.

Example 40

The prosthetic heart valve according to any example herein, particularly example 39, wherein the commissure tab assemblies are coupled to the commissure windows via respective tab portions on a radially-outer side of the frame.

Example 41

The prosthetic heart valve according to any example herein, particularly any of examples 39-40, wherein, for each commissure tab assembly, portions of the tabs of the leaflets disposed on a radially-outer side of the frame are coupled to one or more struts of the respective commissure window by one or more sutures.

Example 42

The prosthetic heart valve according to any example herein, particularly any of examples 32-41, wherein each commissure tab assembly comprises a coupling member that wraps around portions of the tabs of the leaflets.

Example 43

The prosthetic heart valve according to any example herein, particularly example 42, wherein the coupling member comprises a flexible cloth or fabric.

Example 44

The prosthetic heart valve according to any example herein, particularly any of examples 32-38, wherein the frame comprises a plurality of struts that define a plurality of open cells, and the tabs of each commissure tab assembly are coupled by a respective coupling member to struts that surround and define a respective one of the open cells.

Example 45

The prosthetic heart valve according to any example herein, particularly example 44, wherein, for each commissure tab assembly: the tabs thereof are separated and folded to form a T-shape, such that each tab comprises a first portion that extends along a circumferential direction of the frame and contacts the coupling member, and a second portion that extends along a radial direction of the frame, contacts the corresponding second portion of the other tab of the pair, and connects the first portion to a central portion of the leaflet; and each first portion of the tabs is attached to the coupling member by one or more first sutures.

Example 46

The prosthetic heart valve according to any example herein, particularly any of examples 44-45, each coupling member is coupled to the struts by one or more second sutures.

Example 47

The prosthetic heart valve according to any example herein, particularly any of examples 44-46, wherein the coupling member comprises a flexible cloth or fabric.

Example 48

The prosthetic heart valve according to any example herein, particularly any of examples 44-47, wherein the open cells are at an outflow end of the prosthetic heart valve.

Example 49

The prosthetic heart valve according to any example herein, particularly any of examples 32-48, wherein: the frame comprises a plurality of interconnected and angled struts defining a plurality of rows of cells arranged between the outflow end and the inflow end of the frame, and each strut is connected to other struts at intermediate and end portions by respective fasteners, such that the struts can pivot about each fastener to transition between the crimped and expanded configurations.

Example 50

The prosthetic heart valve according to any example herein, particularly any of examples 32-48, wherein the frame comprises a plurality of integrally-formed and angled struts defining a plurality of rows of cells arranged between the outflow end and the inflow end of the frame.

Example 51

The prosthetic heart valve according to any example herein, particularly any of examples 32-48, wherein the frame comprises: a plurality of interconnected and angled struts; and a plurality of commissure support portions, each commissure support portion being arranged on one of a support post, actuator, or expansion/locking mechanism of the frame, each commissure tab assembly being coupled to a corresponding one of the commissure support portions.

Example 52

The prosthetic heart valve according to any example herein, particularly any of examples 32-48, wherein the frame comprises a plurality of support members integrally formed with or coupled to struts of the frame, and each support member comprises a commissure window, each commissure tab assembly being coupled to a corresponding one of the commissure windows to support the valvular structure within the frame.

Example 53

The prosthetic heart valve according to any example herein, particularly example 52, wherein the frame comprises an actuator constructed to expand or contract the frame, or a locking mechanism constructed to maintain a shape of the frame after expansion or contraction thereof, and at least one of the support members is a portion of the actuator or locking mechanism, or is coupled to the actuator or locking mechanism.

Example 54

The prosthetic heart valve according to any example herein, particularly example 52, wherein the frame comprises a plurality of integral expansion/locking (IEL) mechanisms, each IEL mechanism extending along a radial direction of the frame between struts, the IEL mechanisms being constructed to lock the frame at the expanded configuration or at one or more intermediate configurations between the crimped and expanded configurations.

Example 55

The prosthetic heart valve according to any example herein, particularly any of examples 52-54, wherein the struts include compliant hinges or joints, such that the struts flex at each hinge or joint to transition between the crimped and expanded configurations.

Example 56

The prosthetic heart valve according to any example herein, particularly any of examples 32-55, further comprising a circumferential outer skirt disposed on a radially-outer side of the frame and coupled thereto, the outer skirt being adjacent to the inflow end.

Example 57

The prosthetic heart valve according to any example herein, particularly any of examples 32-56, further comprising a circumferential inner skirt disposed on a radially-inner side of the frame and coupled thereto, the inner skirt being adjacent to the inflow end, wherein each leaflet is coupled to the inner skirt at respective cusp edge portions.

Example 58

The prosthetic heart valve according to any example herein, particularly any of examples 32-57, wherein the valvular structure is a bicuspid structure with two leaflets and two commissure tab assemblies, and the valvular structure is coupled to the frame via the commissure tab assemblies on diametrically opposite sides of the frame from each other.

Example 59

The prosthetic heart valve according to any example herein, particularly any of examples 32-58, wherein the valvular structure is a tricuspid structure with three leaflets and three commissure tab assemblies, and the valvular structure is coupled to the frame via the three commissure tab assemblies equally spaced along a circumferential direction of the frame.

Example 60

The prosthetic heart valve according to any example herein, particularly any of examples 1-59, wherein the frame is formed of a plastically-expandable material or a self-expanding material.

Example 61

An assembly for implanting a prosthetic heart valve in a patient's body comprises a delivery apparatus comprising an elongated shaft; and the prosthetic heart valve of any one of examples 1-60 mounted on the elongated shaft in the crimped configuration for delivery into the patient's body.

Example 62

A method of implanting a prosthetic heart valve in a patient's body comprises inserting a distal end of a delivery apparatus into vasculature of a patient, the delivery apparatus comprising an elongated shaft, the prosthetic heart valve of any one of examples 1-60 being releasably mounted in the crimped configuration on the elongated shaft of the delivery apparatus; advancing the prosthetic heart valve to a desired implantation site; and using the delivery apparatus to radially expand the prosthetic heart valve to the expanded configuration, thereby implanting the prosthetic heart valve at the desired implantation site.

Example 63

The method of any example herein, particularly example 62, wherein the advancing to the desired implantation site employs transfemoral, transventricular, transapical, or transseptal approaches.

Example 64

A method of assembling a prosthetic heart valve comprising a plurality of leaflets, the method comprises forming a plurality of tab assemblies with the plurality of leaflets, each leaflet having two tabs arranged on opposite sides of a body of the leaflet, each commissure tab assembly including a pair of tabs from adjacent leaflets; and coupling each commissure tab assembly, either directly or via a coupling member, to a respective portion of a valve frame. The valve frame has an inverted frustoconical shape, with a first diameter at a first end being greater than a second diameter at an opposite second end. A taper angle of the inverted frustoconical shape of the valve frame is 6-8°, inclusive. The valve frame has an end-to-end height that is less than second diameter. A ratio of the end-to-end height of the valve frame to the second diameter is 0.63-0.9, inclusive. The commissure tab assemblies are coupled to the respective portions of the valve frame at axial locations where, when the prosthetic heart valve is implanted, an annular back flow region is generated during systole by blood flowing through a flow channel formed by the leaflets, the annular back flow region being adjacent to a radially-inner circumferential surface of the valve frame.

Example 65

The method of any example herein, particularly example 64, wherein the coupling is such that a bending axis for each leaflet tab is disposed at or substantially adjacent to the radially-inner circumferential surface of the valve frame.

Example 66

The method of any example herein, particularly any of examples 64-65, wherein a ratio of the first diameter to the end-to-end height is less than 1.75.

Example 67

The method of any example herein, particularly any of examples 64-66, wherein a ratio of the first diameter to the end-to-end height is 1.2-1.73, inclusive.

Example 68

The method of any example herein, particularly any of examples 64-67, wherein the forming a plurality of commissure tab assemblies and the coupling each commissure tab assembly are such that the flow channel formed during systole has a tapered profile with a cross-sectional area that expands from an inlet end of the flow channel to an outlet end of the flow channel.

Example 69

The method of any example herein, particularly any of examples 64-68, wherein the coupling each commissure tab assembly comprises inserting tabs of the commissure tab assembly through a respective one of a plurality of commissure windows, such that first portions of the tabs are disposed on a radially-outer side of the valve frame; and using one or more sutures to attach the first portions of the tabs to struts forming the respective commissure window, each commissure window being integrally formed within the valve frame or being formed in a support member, actuator, or locking mechanism that is coupled to the valve frame.

Example 70

The method of any example herein, particularly example 69, wherein the coupling each commissure tab assembly further comprises prior to or after the inserting tabs, wrapping a coupling member around exposed surfaces of the first portions of the tabs, and the one or more sutures passes through a first portion of the coupling member, the first portion of one of the tabs, a second portion of the coupling member, and one of the struts forming the respective commissure window, in order from the radially-outer side to a radially-inner side of the valve frame.

Example 71

The method of any example herein, particularly any of examples 64-68, wherein the valve frame comprises a plurality of struts that define a plurality of open cells, and the coupling each commissure tab assembly comprises: disposing a coupling member within a respective one of the open cells so as to extend between surrounding struts that define the respective open cell; using one or more first sutures to attach the coupling member to the surrounding; and before or after the disposing, using one or more second sutures to attach the tabs to the coupling member.

Example 72

The method of any example herein, particularly example 71, further comprising, prior to the using one or more second sutures, separating and folding the tabs of each commissure tab assembly to form a T-shape, such that each tab comprises a first portion that extends along a circumferential direction of the valve frame and contacts the coupling member, and a second portion that extends along a radial direction of the valve frame, contacts the corresponding second portion of the other tab of the commissure tab assembly, and connects the first portion to a central portion of the leaflet.

Example 73

The method of any example herein, particularly any of examples 69-72, wherein the coupling member comprises a flexible cloth or fabric.

Example 74

The method of any example herein, particularly any of examples 64-73, further comprising coupling a circumferential outer skirt to the valve frame, the circumferential outer skirt being disposed at or adjacent to the second end of the valve frame and on a radially-outer side of the valve frame.

Example 75

The method of any one of examples 64-74, further comprising coupling a circumferential inner skirt to the valve frame, the circumferential inner skirt being disposed at or adjacent to the second end of the valve frame and on a radially-inner side of the valve frame.

Example 76

The method of any example herein, particularly example 75, further comprising coupling a cusp edge portion of each leaflet to the circumferential inner skirt.

Example 77

A prosthetic heart valve comprises a frame having an inflow end and an outflow end spaced along an axial direction of the frame, the frame expandable between a crimped configuration and an expanded configuration; and a valvular structure comprising a plurality of leaflets and a plurality of commissure tab assemblies coupling the valvular structure to the frame, the valvular structure having an open configuration in which free edges of the leaflets part to allow blood flow through the frame and a closed configuration in which the free edges of the leaflets coapt to prevent blood flow through the frame. The frame has a tapered shape in the expanded configuration with a taper in a direction from the outflow end to the inflow end and a taper angle in a range from 6-8°. A ratio of a height of the frame along the axial direction in the expanded configuration to a diameter of the frame at the inflow end in the expanded configuration is in a range from 0.63-0.9. In the expanded configuration of the frame and the open configuration of the valvular structure, the leaflets form a tapered flow channel extending from the inflow end to the outflow end of the frame.

The subject matter has been described with a selection of implementations and examples, but these preferred implementations and examples are not to be taken as limiting the scope of the subject matter since many other implementations and examples are possible that fall within the scope of the subject matter. Accordingly, the scope of the subject matter is defined by the claims.

The invention claimed is:

1. A prosthetic heart valve comprising:
   a frame that is expandable between a crimped configuration and an expanded configuration; and
   a valvular structure comprising a plurality of leaflets, each leaflet having a pair of tabs, the tabs of the pair being on opposite sides from each other with respect to a centerline of the leaflet, the valvular structure having a plurality of commissure tab assemblies formed by paired tabs of adjacent leaflets, the valvular structure being coupled to the frame via the plurality of commissure tab assemblies;
   wherein the frame has an inflow end and an outflow end separated from the inflow end along an axial direction of the frame, the inflow end of the frame having a first diameter in the crimped configuration and a second diameter greater than the first diameter in the expanded configuration, the outflow end of the frame having a third diameter in the crimped configuration and a fourth diameter greater than the third diameter in the expanded configuration,
   wherein the frame in the expanded configuration has an inverted frustoconical shape, with the fourth diameter of the outflow end being greater than the second diameter of the inflow end,
   wherein a taper angle of the inverted frustoconical shape of the frame in the expanded configuration is within a range of 6-8°,
   wherein the frame in the expanded configuration has a height along the axial direction from the inflow end to the outflow end,
   wherein a ratio of the height of the frame in the expanded configuration to the second diameter of the inflow end is within a range of 0.63-0.9,
   wherein the valvular structure is constructed to transition between a closed configuration, where the leaflets prevent blood flow from the inflow end to the outflow end of the frame, and an open configuration, where the leaflets deflect away from a central axis of the frame to form a flow channel from the inflow end to the outflow end of the frame, and
   wherein the flow channel formed by the valvular structure in the open configuration is tapered such that a cross-sectional area at an outlet of the flow channel is greater than a cross-sectional area at an inlet of the flow channel.

2. The prosthetic heart valve of claim 1, wherein the prosthetic heart valve is constructed such that blood flow through the flow channel of the valvular structure in the open configuration produces an annular back flow region adjacent to a radially-inner circumferential surface of the frame, and the commissure tab assemblies are positioned at respective locations along the axial direction within the annular back flow region.

3. The prosthetic heart valve of claim 1, wherein in transitioning between the open configuration and the closed configuration, each leaflet bends about a respective bending axis, and each bending axis is disposed at or substantially adjacent to a radially-inner circumferential surface of the frame where the valvular structure is coupled via the respective commissure tab assembly.

4. The prosthetic heart valve of claim 1, wherein a ratio of the fourth diameter of the outflow end to the height of the frame is less than 1.75.

5. The prosthetic heart valve of claim 1, wherein the ratio of the fourth diameter of the outflow end to the height of the frame is within a range of 1.2-1.73.

6. The prosthetic heart valve of claim 1, wherein the cross-sectional area of the flow channel varies in a substantially linear manner along the axial direction from the inlet of the flow channel to the outlet of the flow channel.

7. The prosthetic heart valve of claim 1, wherein the flow channel extends substantially parallel to and coaxial with the frame.

8. The prosthetic heart valve of claim 1, wherein the frame comprises a plurality of commissure windows, and each commissure tab assembly is coupled to a corresponding one of the commissure windows to support the valvular structure within the frame.

9. The prosthetic heart valve of claim 8, wherein the commissure tab assemblies are coupled to the commissure windows via respective tab portions on a radially-outer side of the frame.

10. The prosthetic heart valve of claim 1, wherein the frame comprises a plurality of struts that define a plurality of open cells, and wherein the frame comprises a plurality of integrally-formed and angled struts defining a plurality of rows of cells arranged between the outflow end and the inflow end of the frame.

11. The prosthetic heart valve of claim 1, wherein the frame comprises a plurality of support members integrally formed with or coupled to struts of the frame, each support member comprising a commissure window, each commissure tab assembly being coupled to a corresponding one of the commissure windows to support the valvular structure within the frame.

12. The prosthetic heart valve of claim 1, further comprising at least one of (a) a circumferential outer skirt disposed on a radially-outer side of the frame and coupled thereto, the outer skirt being at or adjacent to the inflow end and (b) a circumferential inner skirt disposed on a radially-inner side of the frame and coupled thereto, the inner skirt being at or adjacent to the inflow end, wherein each leaflet is coupled to the inner skirt at respective cusp edge portions.

13. An assembly for implanting a prosthetic heart valve in a patient's body, the assembly comprising:
a delivery apparatus comprising an elongated shaft; and
the prosthetic heart valve of claim 1 mounted on the elongated shaft in the crimped configuration for delivery into the patient's body.

14. A method of implanting a prosthetic heart valve in a patient's body, the method comprising:
inserting a distal end of a delivery apparatus into vasculature of a patient, the delivery apparatus comprising an elongated shaft, the prosthetic heart valve of claim 1 being releasably mounted in the crimped configuration on the elongated shaft of the delivery apparatus;
advancing the prosthetic heart valve to a desired implantation site; and
using the delivery apparatus to radially expand the prosthetic heart valve to the expanded configuration, thereby implanting the prosthetic heart valve at the desired implantation site.

15. A method of assembling a prosthetic heart valve comprising a plurality of leaflets, the method comprising:
forming a plurality of tab assemblies with the plurality of leaflets, each leaflet having two tabs arranged on opposite sides of a body of the leaflet, each commissure tab assembly including a pair of tabs from adjacent leaflets; and
coupling each commissure tab assembly, either directly or via a coupling member, to a respective portion of a valve frame;
wherein the valve frame has an inverted frustoconical shape, with a first diameter at a first end being greater than a second diameter at an opposite second end,
wherein a taper angle of the inverted frustoconical shape of the valve frame is in a range from 6-8°,
wherein the valve frame has an end-to-end height that is less than the second diameter,
wherein a ratio of the end-to-end height of the valve frame to the second diameter is in a range from 0.63-0.9, and
wherein the commissure tab assemblies are coupled to the respective portions of the valve frame at axial locations where, when the prosthetic heart valve is implanted, an annular back flow region is generated during systole by blood flowing through a flow channel formed by the leaflets, the annular back flow region being adjacent to a radially-inner circumferential surface of the valve frame.

16. The method of claim 15, wherein a ratio of the first diameter to the end-to-end height is less than 1.75.

17. The method of claim 15, wherein a ratio of the first diameter to the end-to-end height is within a range of 1.2-1.73.

18. The method of claim 15, further comprising at least one of (a) coupling a circumferential outer skirt to the valve frame, the circumferential outer skirt being disposed at or adjacent to the second end of the valve frame and on a radially-outer side of the valve frame and (b) coupling a circumferential inner skirt to the valve frame, the circumferential inner skirt being disposed at or adjacent to the second end of the valve frame and on a radially-inner side of the valve frame.

19. A prosthetic heart valve comprising:
a frame having an inflow end and an outflow end spaced along an axial direction of the frame, the frame expandable between a crimped configuration and an expanded configuration; and
a valvular structure comprising a plurality of leaflets and a plurality of commissure tab assemblies coupling the valvular structure to the frame, the valvular structure having an open configuration in which free edges of the leaflets part to allow blood flow through the frame and a closed configuration in which the free edges of the leaflets coapt to prevent blood flow through the frame;

wherein the frame has a tapered shape in the expanded configuration with a taper in a direction from the outflow end to the inflow end and a taper angle in a range from 6-8°;

wherein a ratio of a height of the frame along the axial direction in the expanded configuration to a diameter of the frame at the inflow end in the expanded configuration is in a range from 0.63-0.9; and wherein in the expanded configuration of the frame and the open configuration of the valvular structure the leaflets form a tapered flow channel extending from the inflow end to the outflow end of the frame.

\*  \*  \*  \*  \*